(12) United States Patent
Seimori et al.

(10) Patent No.: US 10,048,097 B2
(45) Date of Patent: Aug. 14, 2018

(54) GAS SENSOR

(71) Applicant: NGK INSULATORS, LTD., Nagoya-shi, Aichi (JP)

(72) Inventors: Tomoya Seimori, Nagoya (JP); Mika Murakami, Nagoya (JP); Kengo Takeuchi, Handa (JP)

(73) Assignee: NGK INSULATORS, LTD., Nagoya (JP)

( * ) Notice: Subject to any disclaimer, the term of this patent is extended or adjusted under 35 U.S.C. 154(b) by 49 days.

(21) Appl. No.: 14/955,369

(22) Filed: Dec. 1, 2015

(65) Prior Publication Data

US 2016/0153814 A1   Jun. 2, 2016

(30) Foreign Application Priority Data

Dec. 2, 2014   (JP) ................................. 2014-244089
Dec. 1, 2015   (JP) ................................. 2015-235040

(51) Int. Cl.
  *G01D 11/24*   (2006.01)
  *G01N 27/407*   (2006.01)
  *G01N 33/00*   (2006.01)

(52) U.S. Cl.
  CPC ....... *G01D 11/245* (2013.01); *G01N 27/4077* (2013.01); *G01N 33/0054* (2013.01); *Y02A 50/246* (2018.01)

(58) Field of Classification Search
  CPC ... G01N 27/4077; G01D 11/24; G01D 11/245
  See application file for complete search history.

(56) References Cited

U.S. PATENT DOCUMENTS

2008/0223110 A1    9/2008   Weyl et al.
2011/0011152 A1*   1/2011   Ito ...................... G01N 27/4074
                                                    73/23.31
(Continued)

FOREIGN PATENT DOCUMENTS

DE    102006044430 A1 *  4/2008  ......... G01N 27/4077
EP         2154524 A2       2/2010
(Continued)

OTHER PUBLICATIONS

The Extended European Search Report for the corresponding European patent application No. 15197505.9 dated Mar. 24, 2016.
(Continued)

*Primary Examiner* — Lisa Caputo
*Assistant Examiner* — Jamel Williams
(74) *Attorney, Agent, or Firm* — Global IP Counselors, LLP

(57) ABSTRACT

A gas sensor includes a sensor element that includes a gas inlet through which a measurement target gas is introduced into the sensor element and a protective cover that contains a substance having a capability of decomposing ammonia. The protective cover has a gas-contact surface area within a range of 450 mm$^2$ to 1145 mm$^2$, the gas-contact surface area being a sum of a surface area of a portion facing the inlet-side gas flow path and a surface area of a portion facing an in-element-chamber flow path of the sensor element chamber that is a shortest flow path for the measurement target gas from the element-chamber inlet to the gas inlet.

6 Claims, 12 Drawing Sheets

(56) References Cited

U.S. PATENT DOCUMENTS

| | | | |
|---|---|---|---|
| 2011/0283775 A1* | 11/2011 | Sekiya | G01N 27/4077 |
| | | | 73/31.05 |
| 2012/0111092 A1 | 5/2012 | Nakashima | |
| 2013/0305809 A1* | 11/2013 | Fujita | G01N 27/4077 |
| | | | 73/31.05 |
| 2015/0052973 A1* | 2/2015 | Nakashima | G01D 11/245 |
| | | | 73/23.2 |
| 2015/0253282 A1* | 9/2015 | Satou | G01N 27/4071 |
| | | | 204/429 |

FOREIGN PATENT DOCUMENTS

| | | |
|---|---|---|
| EP | 2 184 601 A2 | 5/2010 |
| EP | 2278316 A1 | 1/2011 |
| EP | 2333534 A2 | 6/2011 |
| JP | 3511468 B2 | 1/2004 |
| JP | 5469553 B2 | 2/2014 |
| WO | 2010/015445 A1 | 2/2010 |
| WO | 2014/192945 A1 | 12/2014 |

OTHER PUBLICATIONS

The Office Action for the corresponding European application No. 15 197 505.9 dated Jun. 30, 2017.

\* cited by examiner

GAS SENSOR

BACKGROUND OF THE INVENTION

1. Field of the Invention

The present invention relates to gas sensors.

2. Description of the Related Art

To date, use of urea as a reducing agent is known as a method for purging NOx from exhaust gas from diesel engines. For example, PTL 1 describes a configuration in which an injector, which injects urea into an exhaust pipe, a selective catalytic reduction (SCR) catalyst, which reduces nitrogen oxide (NOx) using ammonia produced at the time of hydrolysis of urea so that Nox is converted into harmless $N_2$ and $H_2O$, and an ammonia-concentration sensor, which detects an excessive ammonia concentration contained in the exhaust gas that has passed the SCR catalyst, are disposed on an engine exhaust path. PTL 1 also describes that the rate of urea injected into the exhaust pipe from the injector is controlled so that the ammonia concentration detected by the ammonia-concentration sensor becomes closer to zero. The ammonia-concentration sensor includes a sensor element, formed by stacking multiple oxygen-ion-conducting solid electrolyte layers one on top of another, and a protective cover, which controls flow of gas to the sensor element or prevents water from adhering to the sensor element. PTL 1 describes that coating the protective cover with a coating layer prevents ammonia from being decomposed by the protective cover so that degradation of the ammonia-concentration detection sensitivity is suppressed.

CITATION LIST

Patent Literature

PTL 1: Japanese Patent No. 5469553

SUMMARY OF THE INVENTION

The ammonia-concentration sensor described in PTL 1, however, requires a process of coating the protective cover to prevent decomposition of ammonia. Thus, a method for preventing decomposition of ammonia other than coating has been awaited.

The present invention was made to solve such problems and a main purpose of the invention is to prevent ammonia in a measurement target gas from being decomposed by a protective cover.

The present invention employs the following means for achieving the above-described main purpose.

A gas sensor according to the present invention comprising:

a sensor element that includes a gas inlet through which a measurement target gas is introduced into the sensor element, the sensor element being capable of detecting a predetermined gas concentration of the measurement target gas that has flowed into an inside of the sensor element through the gas inlet; and a protective cover that contains a substance having a capability of decomposing ammonia, the protective cover defining a sensor element chamber and an inlet-side gas flow path, the sensor element chamber being a chamber in which a front end of the sensor element and the gas inlet are disposed, the inlet-side gas flow path including one or more element-chamber inlets serving as inlets to the sensor element chamber, the inlet-side gas flow path extending from an outside to the sensor element chamber, wherein the protective cover has a gas-contact surface area S within a range of 450 $mm^2$ to 1145 $mm^2$, the gas-contact surface area S being a sum of a surface area S1 of a portion facing the inlet-side gas flow path and a surface area S2 of a portion facing an in-element-chamber flow path in the sensor element chamber that is a shortest flow path for the measurement target gas from the element-chamber inlet to the gas inlet.

In this gas sensor, the protective cover contains a substance that has a capability of decomposing ammonia. The protective cover, however, has a gas-contact surface area S within the range from 450 $mm^2$ to 1145 $mm^2$, where the gas-contact surface area S is the sum of a surface area S1 of a portion facing an inlet-side gas flow path and a surface area S2 of a portion facing an in-element-chamber flow path. When the gas-contact surface area S is determined to be 1145 $mm^2$ or less, the area over which the measurement target gas touches the protective cover from when it passes through the inside of the protective cover until when it arrives at a gas inlet of the sensor element is reduced to a sufficiently small level. This configuration can thus prevent ammonia in the measurement target gas from being decomposed by the protective cover. When the gas-contact surface area S is determined to be 450 $mm^2$ or more, failures resulting from simplifying the path for the measurement target gas from when it passes through the inside of the protective cover until when it arrives at a gas inlet of the sensor element can be prevented. Examples of failures resulting from simplifying the path for the measurement target gas include facilitation of arrival of external poisoned substances or water to the sensor element. Here, "the capability of decomposing ammonia" means a capability of converting ammonia into a substance/substances other than ammonia, such as nitrogen ($N_2$), NOx, hydrogen ($H_2$), or water ($H_2O$). The element-chamber inlet may be a hole formed in the protective cover or a gap between multiple components constituting the protective cover. As the gas-contact surface area S is decreasing, the effect of suppressing decomposition of ammonia in the measurement target gas by the protective cover is enhanced. In this respect, the gas-contact surface area S may be, for example, 1100 $mm^2$ or less, 1050 $mm^2$ or less, 1040 $mm^2$ or less, 1000 $mm^2$ or less, 950 $mm^2$ or less, 900 $mm^2$ or less, 850 $mm^2$ or less, or 800 $mm^2$ or less. As the gas-contact surface area S is increasing, failures resulting from simplifying the path for the measurement target gas are more likely to be suppressed. In this respect, the gas-contact surface area S is preferably, for example, 500 $mm^2$ or more, 550 $mm^2$ or more, 600 $mm^2$ or more, 650 $mm^2$ or more, and may be 700 $mm^2$ or more or 750 $mm^2$ or more.

In the gas sensor according to the present invention, the protective cover defines an outlet-side gas flow path extending to the outside from the sensor element chamber and including one or more element-chamber outlets serving as outlets from the sensor element chamber. The protective cover may define the one or more element-chamber inlets at a position spaced apart from the gas inlet a distance A1 of −1.5 mm or more, where the distance A1 is a distance extending in a direction connecting the rear end and the front end of the sensor element where the direction from the front end to the rear end is regarded as a positive direction, and the one or more element-chamber outlets at a position located away from the gas inlet in a direction toward a front end from a rear end of the sensor element. In the case where the one or more element-chamber outlets are located away from the gas inlet in the direction toward the front end from the rear end of the sensor element and the distance A1 is less than −1.5 mm, the measurement target gas fails to flow smoothly and is likely to stagnate at a portion of the sensor element chamber around the gas inlet. When the measurement target gas stagnates, the time period for which the measurement target gas and the protective cover touch each other increases, whereby ammonia in the measurement target gas is likely to be decomposed. In the case where the distance A1 is −1.5 mm or more, the measurement target gas smoothly flows, whereby ammonia in the measurement target gas can be prevented from being decomposed by the protective cover. In this case, the distance A1 may be determined to be 0 mm or more or may exceed 1.5 mm.

In the gas sensor according to the present invention, the protective cover may define an outlet-side gas flow path extending to the outside from the sensor element chamber and including one or more element-chamber outlets serving as outlets from the sensor element chamber. The protective cover may include an inner protective cover and an outer protective cover disposed on the outer side of the inner protective cover. The inner protective cover may define the sensor element chamber, the one or more element-chamber inlets, and the one or more element-chamber outlets. The outer protective cover may define one or more outer inlets, which serve as inlets for the measurement target gas from the outside and constitute part of the inlet-side gas flow path, and one or more outer outlets, which serve as outlets for the measurement target gas to the outside and constitute part of the outlet-side gas flow path. The outer protective cover and the inner protective cover may define a first gas chamber and a second gas chamber. The first gas chamber is a space between the covers, constitutes part of the inlet-side gas flow path, and is located between the one or more outer inlets and the one or more element-chamber inlets. The second gas chamber is a space between the covers, constitutes part of the outlet-side gas flow path, is located between the one or more outer outlets and the one or more element-chamber outlets, and does not directly communicate with the first gas chamber.

In this case, the inner protective cover may define the one or more element-chamber outlets at a position located away from the one or more element-chamber inlets in a direction toward the front end from the rear end of the sensor element. The outer protective cover may include a cylindrical barrel, in which the one or more outer inlets are formed, and a bottomed cylindrical front end portion, in which the one or more outer outlets located at a position closer to the front end of the sensor element than to the one or more outer inlets are formed. The bottomed cylindrical front end portion has an inner diameter smaller than that of the barrel. The outer protective cover and the inner protective cover may define the first gas chamber between the barrel of the outer protective cover and the inner protective cover and may define the second gas chamber between the front end portion of the outer protective cover and the inner protective cover.

In the gas sensor according to the present invention, the area ratio α may fall within the range from 12 to 35, where the area ratio α=a cross-sectional area G2×a cross-sectional area G3×a cross-sectional area G4/a cross-sectional area G1, where the cross-sectional area G1 is the sum of the cross-sectional areas of the one or more outer inlets taken perpendicularly to the flow of the measurement target gas, the cross-sectional area G2 is the sum of the cross-sectional areas of the one or more element-chamber inlets taken perpendicularly to the flow of the measurement target gas, the cross-sectional area G3 is the sum of the cross-sectional areas of the one or more element-chamber outlets taken perpendicularly to the flow of the measurement target gas, and the cross-sectional area G4 is the sum of the cross-sectional areas of the one or more outer outlets taken perpendicularly to the flow of the measurement target gas. As the area ratio α increases, the cross-sectional areas G2, G3, and G4 of the one or more element-chamber inlets, the one or more element-chamber outlets, and the one or more outer outlets increase with respect to the cross-sectional areas G1 of the one or more outer inlets, whereby the measurement target gas is more likely to flow smoothly in the protective cover. In the case where the area ratio α is 13 or more, the measurement target gas flows very smoothly in the protective cover and the time period for which the measurement target gas touches the protective cover until it arrives at the gas inlet of the sensor element is shortened. Thus, ammonia in the measurement target gas can be prevented from being decomposed by the protective cover. In the case where the area ratio α is 27 or less, cooling of the sensor element due to an excessively high flow rate of the measurement target gas can be suppressed, whereby cracking of the sensor element can be suppressed. As the area ratio α is increasing, the effect of suppressing decomposition of ammonia in the measurement target gas by the protective cover is enhanced. In this respect, the area ratio α is, for example, preferably 12.79 or more, more preferably 13 or more, still more preferably 18 or more. As the area ratio α is decreasing, the effect of suppressing the cooling of the sensor element is enhanced. In this respect, the area ratio α is, for example, preferably 34.20 or less, more preferably 30 or less, still more preferably 27 or less, further still more preferably 24 or less, and may be 20 or less, 19.70 or less.

In the gas sensor according to the present invention, the protective cover may define the one or more element-chamber inlets in such a manner that an element-side opening of each of the one or more element-chamber inlets, which is an opening located closer to the sensor element chamber, is open in the direction extending from the rear end to the front end of the sensor element. Thus, the measurement target gas that has flowed out from the element-side opening can be prevented from vertically coming into contact with the surface of the sensor element, that is, a portion of the surface other than the gas inlet, or prevented from arriving at the gas inlet after flowing a long distance over the surface of the sensor element. Cooling of the sensor element can thus be prevented. Since the cooling of the sensor element is prevented by adjusting the orientation of the opening of the element-side opening instead of reducing the flow rate or the flow speed of the measurement target gas, the responsivity to the gas concentration detection can be prevented from being lowered. These features make the responsivity and the heat retaining property of the sensor element compatible. Here, the element-side opening may be open parallel to the direction connecting the rear end and the front end of the sensor element or may be open obliquely with respect to the direction connecting the rear end and the front end so as to come closer to the sensor element toward the front end from the rear end of the sensor element.

In the gas sensor according to the invention, the protective cover may be formed of a metal containing at least one of chromium or nickel as a substance having a capability of decomposing ammonia. When the protective cover contains at least one of chromium or nickel, the protective cover can have a higher corrosion resistance.

DETAILED DESCRIPTION OF THE INVENTION

Figure 1:
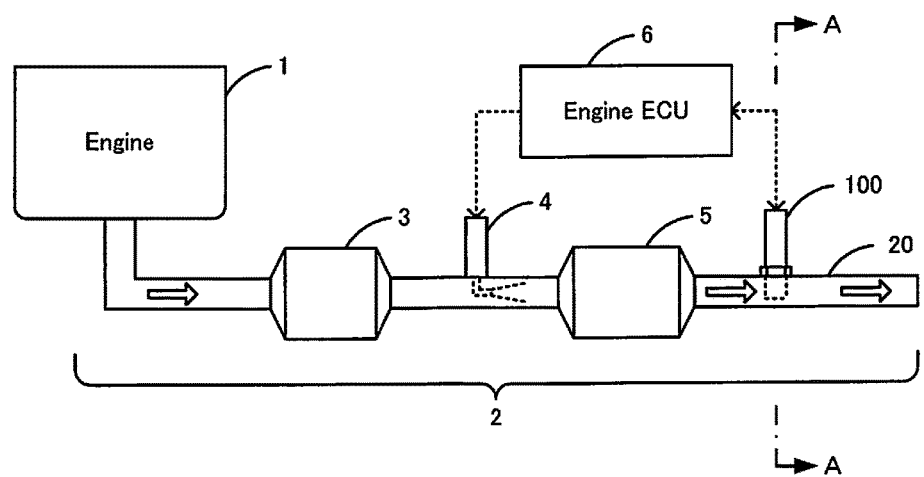
FIG. 1 is a schematic diagram of an exhaust path 2 of an engine 1.
Figure 2:
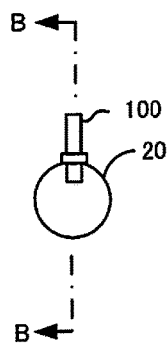
FIG. 2 is a cross-sectional view taken along the line A-A in FIG. 1.

Now, embodiments of the present invention are described referring to the drawings. FIG. 1 is a schematic diagram of an exhaust path 2 of an engine 1. FIG. 2 is a cross-sectional view taken along the line A-A in FIG. 1.

As illustrated in FIG. 1, an oxidation catalyst 3, an injector 4 that injects urea into an exhaust pipe, a selective catalytic reduction (SCR) catalyst 5 that reduces nitrogen oxide (NOx) using ammonia produced at the hydrolysis of urea and decomposes NOx into harmless $N_2$ and $H_2O$, a pipe 20 through which exhaust gas that has passed the SCR catalyst 5 flows, and a gas sensor 100 that is attached to the pipe 20 and that detects the ammonia concentration in the exhaust gas, or measurement target gas, in the pipe 20 are disposed in the exhaust path 2 of the engine 1. The exhaust gas immediately after exhausted from the engine 1 contains substances such as hydrocarbon (HC), carbon monoxide (CO), or NOx. When this exhaust gas passes through the oxidation catalyst 3, HC and CO are detoxified by being converted into water and carbon dioxide but NOx remains as it is even after passing through the oxidation catalyst 3. The SCR catalyst 5 reduces NOx in the exhaust gas that has passed through the oxidation catalyst 3 using ammonia produced after hydrolysis of urea injected from the injector 4 and decomposes NOx into harmless $N_2$ and $H_2O$. The gas sensor 100 detects an excessive ammonia concentration contained in the exhaust gas in the pipe 20 that has passed through the SCR catalyst 5. As illustrated in FIG. 2, the gas sensor 100 is fixed to the inside of the pipe 20 in the state where the center axis of the gas sensor 100 extends perpendicularly to the flow of the measurement target gas in the pipe 20. Here, the gas sensor 100 may be fixed to the inside of the pipe 20 in the state where the center axis of the gas sensor 100 is inclined by a predetermined angle, for example, 45°, with respect to the direction perpendicular to the flow of the measurement target gas in the pipe 20, and the vertical direction in FIG. 2. An engine ECU 6 controls the rate of urea injected from the injector 4 to the exhaust pipe so that the detected excessive ammonia concentration becomes closer to zero. Hereinbelow, the gas sensor 100 is described in detail.

Figure 3:
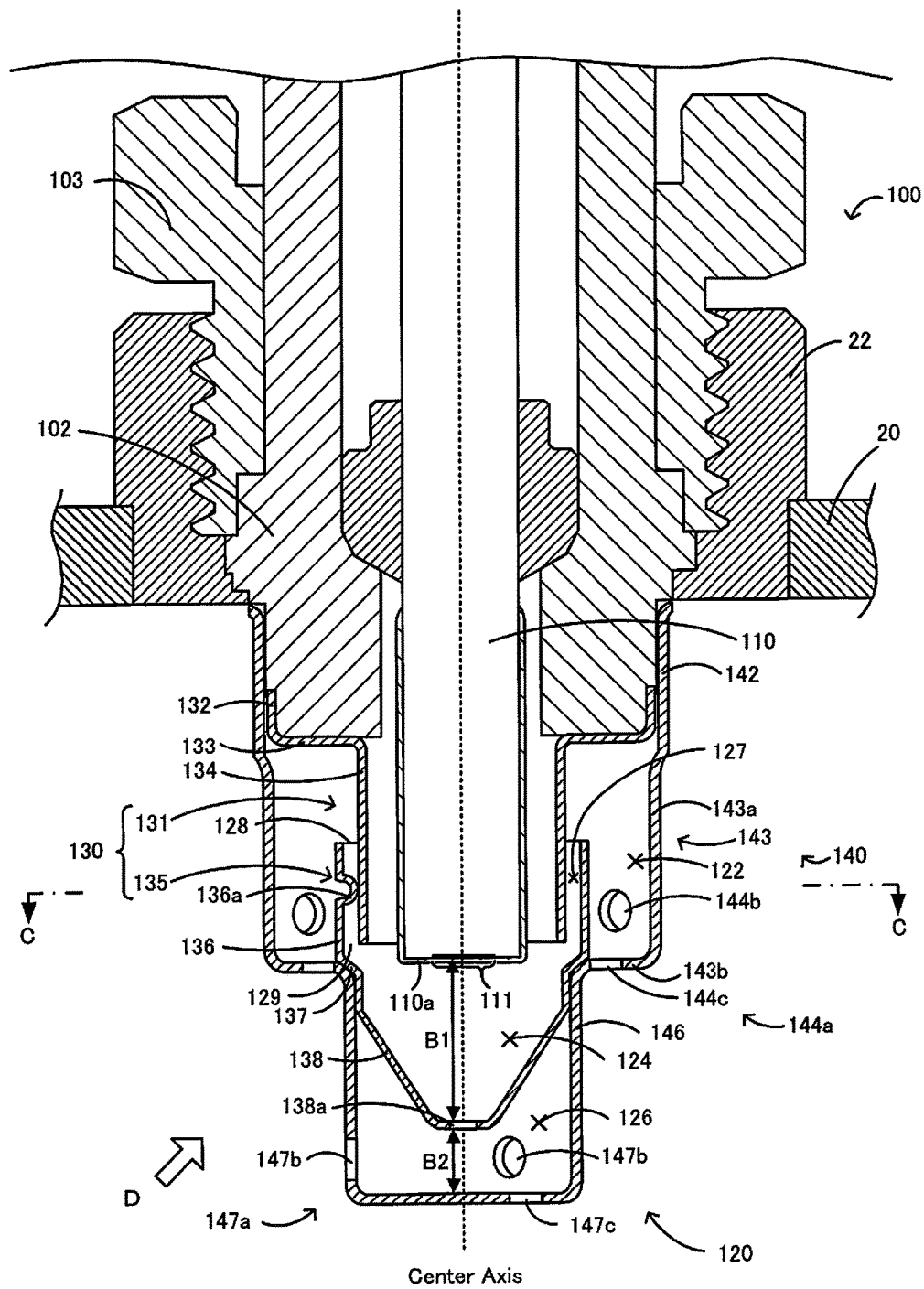
FIG. 3 is a vertical sectional view of the gas sensor 100.
Figure 4:
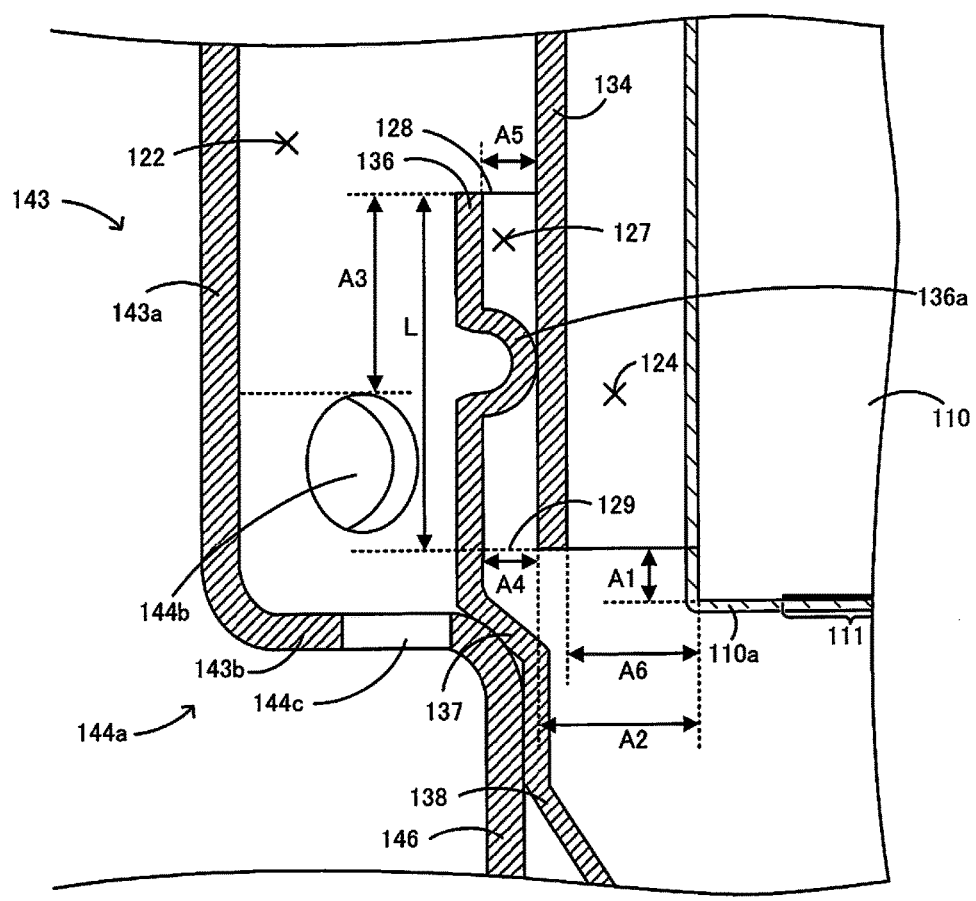
FIG. 4 is an enlarged cross-sectional view of a portion around an element-chamber inlet 127 illustrated in FIG. 3.
Figure 5:
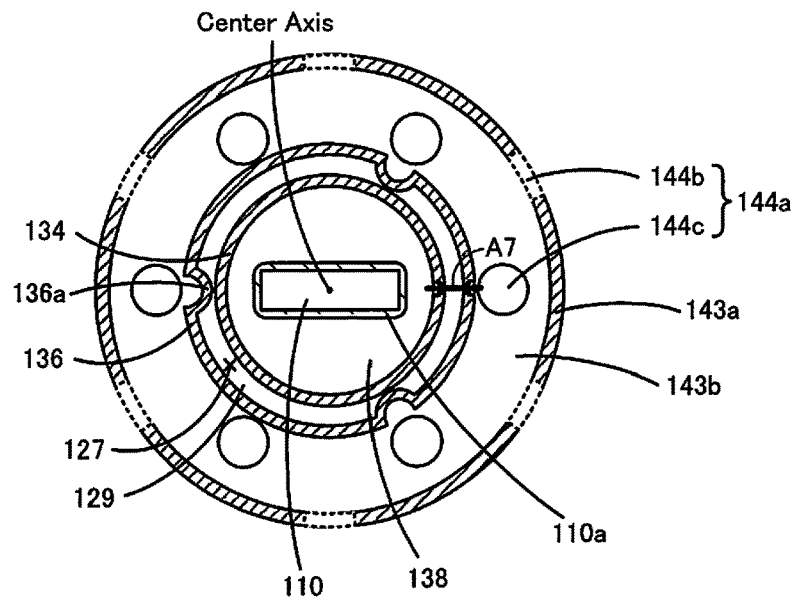
FIG. 5 is a cross-sectional view taken along the line C-C in FIG. 3.
Figure 6:
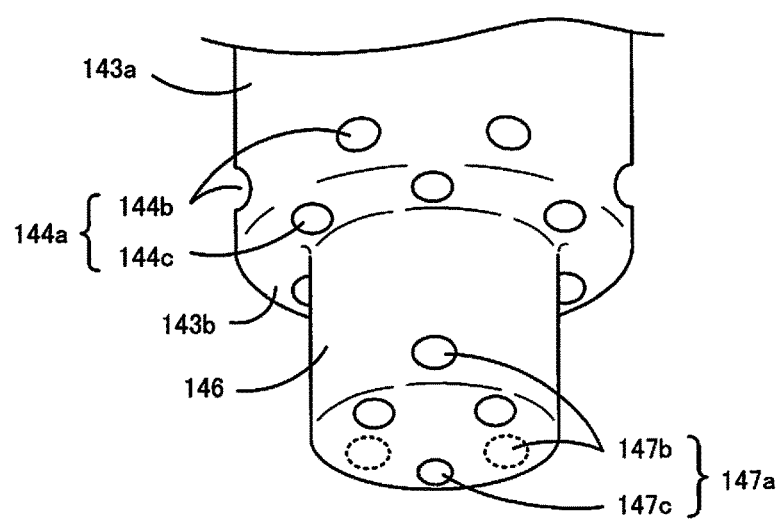
FIG. 6 is a diagram viewed in a direction of arrow D in FIG. 3.
Figure 7:
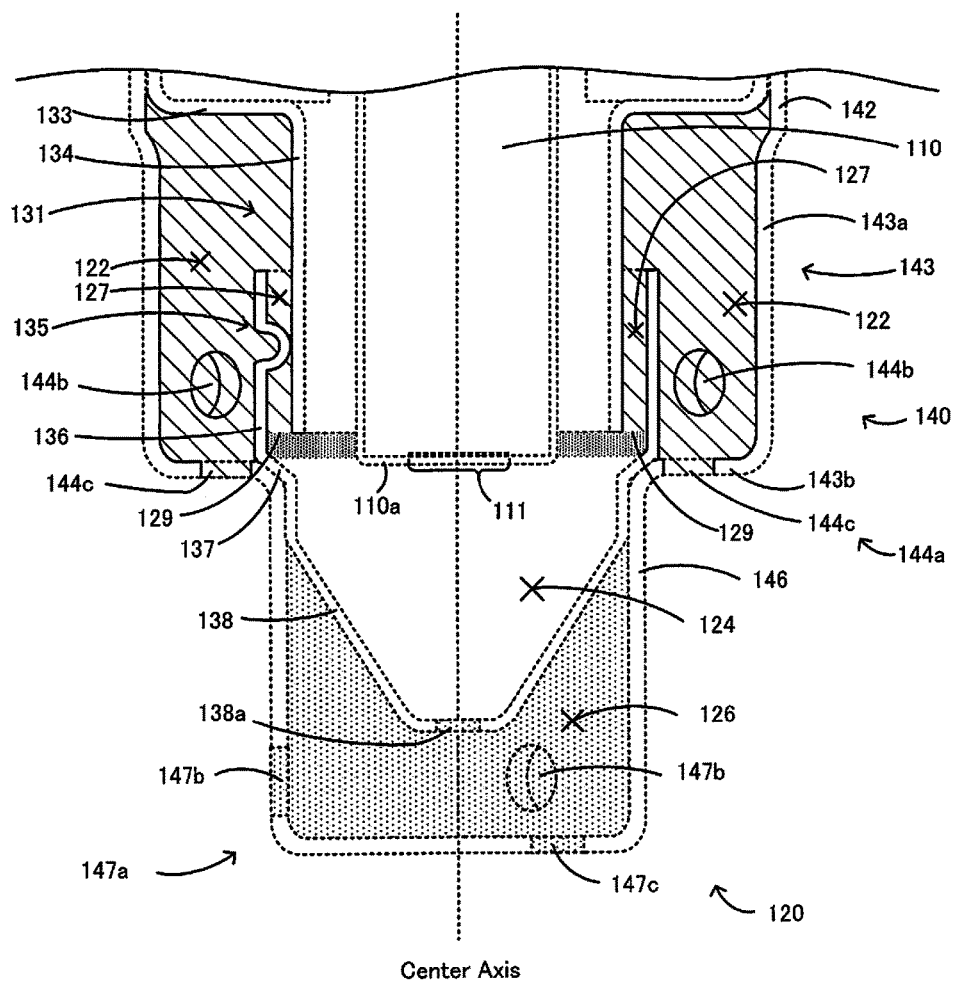
FIG. 7 is a schematic diagram of an inlet-side gas flow path 150, an in-element-chamber flow path 152, and an outlet-side gas flow path 154.

FIG. 3 is a cross-sectional view taken along the line B-B in FIG. 2 and is a vertical sectional view of the gas sensor 100. FIG. 4 is an enlarged cross-sectional view of a portion around an element-chamber inlet 127 illustrated in FIG. 3. FIG. 5 is a cross-sectional view taken along the line C-C in FIG. 3. FIG. 6 is a diagram viewed in a direction of arrow D in FIG. 3. FIG. 7 is a schematic diagram of an inlet-side gas flow path 150, an in-element-chamber flow path 152, and an outlet-side gas flow path 154.

As illustrated in FIG. 3, the gas sensor 100 includes a sensor element 110, which has a function of detecting a predetermined gas concentration or ammonia concentration in the measurement target gas, and a protective cover 120, which protects the sensor element 110. The gas sensor 100 also includes a metal housing 102 and a metal nut 103 having a male thread on its external circumferential surface. The housing 102 is welded to the pipe 20 and inserted into a fixing member 22 having a female thread on its internal circumferential surface. The nut 103 is also inserted into the fixing member 22, so that the housing 102 is fixed to the inside of the fixing member 22. In this manner, the gas sensor 100 is fixed to the inside of the pipe 20. The direction in which the measurement target gas flows in the pipe 20 is the direction from left to right in FIG. 3.

The sensor element 110 is a long thin plate-shaped element and has a configuration in which multiple layers of an oxygen-ion-conducting solid electrolyte such as zirconia ($ZrO_2$) are stacked one on top of another. The sensor element 110 has a gas inlet 111 through which the measurement target gas is introduced into the sensor element 110 and is configured to be capable of detecting a predetermined gas concentration or ammonia concentration of the measurement target gas that has flowed into the sensor element 110 through the gas inlet 111. More specifically, the sensor element 110 detects the ammonia concentration by converting, into NOx, ammonia in the measurement target gas that has flowed into the sensor element 110 through the gas inlet 111 and by detecting the concentration of converted NOx. In this embodiment, the gas inlet 111 is open in the front end surface of the sensor element 110 or in the undersurface of the sensor element 110 in FIG. 3. The sensor element 110 includes a heater within itself, the heater having a temperature adjustment function with which it heats the sensor element 110 and conserves the heat of the sensor element 110. Such a configuration of the sensor element 110 and a principle of gas concentration detection are publicly known and described in, for example, PTL 1, described above. The front end, or the lower end in FIG. 3, and the gas inlet 111 of the sensor element 110 are located inside a sensor element chamber 124.

The sensor element 110 also includes a porous protective layer 110a that covers at least part of the surface of the sensor element 110. In this embodiment, the porous protective layer 110a is disposed over five of six surfaces of the sensor element 110 and covers most part of the surfaces of the sensor element 110 exposed to the sensor element chamber 124. Specifically, the porous protective layer 110a covers the entirety of the front end surface that is, the undersurface in FIG. 3, of the sensor element 110 in which the gas inlet 111 is formed. The porous protective layer 110a also covers portions of the four surfaces connected to the front end surface of the sensor element 110, that is, upper, lower, left, and right surfaces of the sensor element 110 in FIG. 5, the portions being close to the front end surface of the sensor element 110. The porous protective layer 110a has a function of, for example, preventing the sensor element 110 from being cracked as a result of adherence of moisture or other substances in the measurement target gas to the sensor element 110. The porous protective layer 110a also has a function of preventing a component contained in the measurement target gas such as an oil component from adhering to an electrode or other members, not illustrated, on the surface of the sensor element 110. The porous protective layer 110a is formed of a porous body such as an alumina porous body, a zirconia porous body, a spinel porous body, a cordierite porous body, a titania porous body, or a magnesia porous body. The porous protective layer 110a can be formed by, for example, plasma spraying, screen-printing, or dipping. Although the porous protective layer 110a also covers the gas inlet 111, the measurement target gas can arrive at the gas inlet 111 through the inside of the porous protective layer 110a since the porous protective layer 110a is formed of a porous body. For example, the thickness of the porous protective layer 110a may fall within the range of 100 µm to 700 µm, although the thickness is not particularly limited to these values.

The protective cover 120 is disposed so as to surround the sensor element 110. The protective cover 120 includes a bottomed cylindrical inner protective cover 130, which covers the front end of the sensor element 110, and a bottomed cylindrical outer protective cover 140, which covers the inner protective cover 130. A first gas chamber 122 and a second gas chamber 126 are formed as spaces defined by the inner protective cover 130 and the outer protective cover 140. The sensor element chamber 124 is formed as a space defined by the inner protective cover 130. The center axes of the gas sensor 100, the sensor element 110, the inner protective cover 130, and the outer protective cover 140 are coaxial with one another. The protective cover 120 is formed of a metal containing at least one of chromium or nickel, such as stainless steel.

The inner protective cover 130 includes a first member 131 and a second member 135. The first member 131 includes a cylindrical large-diameter portion 132, a first cylindrical portion 134 having a cylindrical shape and a smaller diameter than the large-diameter portion 132, and a stepped portion 133 that connects the large-diameter portion 132 and the first cylindrical portion 134 together. The second member 135 includes a second cylindrical portion 136 having a larger diameter than the first cylindrical portion 134, a front end portion 138 located away from the second cylindrical portion 136 in the direction toward the front end from the rear end of the sensor element 110, lower in FIG. 3, and having a shape of a reversed truncated cone, and a connection portion 137 that connects the second cylindrical portion 136 and the front end portion 138 together. In addition, a circular element-chamber outlet 138a, which is also referred to as an inner gas hole, which communicates with the sensor element chamber 124 and the second gas chamber 126 and serves as an outlet for the measurement target gas from the sensor element chamber 124, is formed in a center portion of the bottom surface of the front end portion 138. For example, the diameter of the element-chamber outlet 138a may fall within the range of 0.5 mm to 2.6 mm, although the diameter is not particularly limited to these values. The element-chamber outlet 138a is formed at a position closer to the front end of the sensor element 110, lower in FIG. 3, than to the gas inlet 111. In other words, the element-chamber outlet 138a is located further, lower in FIG. 3, than the gas inlet 111 when viewed from the rear end of the sensor element 110 or the upper end of the sensor element 110 in FIG. 3, which is not illustrated in FIG. 3. Specifically, the element-chamber outlet 138a is located at a position spaced apart from the gas inlet 111 at a distance B1 (see FIG. 3) smaller than 0 mm. Here, the distance B1 is a distance extending in the direction connecting the rear end and the front end of the sensor element 110, or the vertical direction in FIG. 3, where the direction from the front end to the rear end, that is, the upward direction in FIG. 3 is regarded as a positive direction. The distance B1 is a distance extending in a direction connecting the rear end and the front end of the sensor element 110 and between a portion of the opening end portion of the gas inlet 111 closest to the element-chamber outlet 138a and a portion of the end portion of the element-chamber outlet 138a closest to the gas inlet 111. The distance B1 may be smaller than or equal to the distance A1, described below.

The large-diameter portion 132, the first cylindrical portion 134, the second cylindrical portion 136, and the front end portion 138 have a common center axis. The large-diameter portion 132 has its internal circumferential surface abutting the housing 102, so that the first member 131 is fixed to the housing 102. In the second member 135, the connection portion 137 has its external circumferential surface abutting and fixed to, by welding or other methods, the internal circumferential surface of the outer protective cover 140. The second member 135 may be fixed to the outer protective cover 140 in such a manner that the outer diameter of the front end portion 138 is formed slightly larger than the inner diameter of a front end portion 146 of the outer protective cover 140 and the front end portion 138 is inserted into the front end portion 146 with pressure.

Multiple protrusions 136a are formed on the internal circumferential surface of the second cylindrical portion 136. The protrusions 136a protrude toward the external circumferential surface of the first cylindrical portion 134 and touch the external circumferential surface. As illustrated in FIG. 5, three protrusions 136a are disposed at equal intervals in the circumferential direction of the internal circumferential surface of the second cylindrical portion 136. The protrusions 136a are formed in a substantially hemispherical shape. The presence of the protrusions 136a facilitates stabilizing the positional relationship between the first cylindrical portion 134 and the second cylindrical portion 136. At the time of, for example, an assembly of the gas sensor 100, after the first member 131 is fixed to the housing 102, the second member 135 can be attached to the first member 131 using the protrusions 136a. Thus, in, for example, the subsequent assembly process of the gas sensor 100, such as at the attachment of the outer protective cover 140, the second member 135 can be prevented from falling off the first member 131, so that the assembly of the gas sensor 100 is facilitated. The protrusions 136a preferably press the external circumferential surface of the first cylindrical portion 134 radially inward. In this configuration, the protrusions 136a can more securely fix the positional relationship between the first cylindrical portion 134 and the second cylindrical portion 136. The protrusions 136a may be formed by, for example, pressing the external circumferential surface of the second cylindrical portion 136 toward the center so that part of the internal circumferential surface protrudes. Alternatively, the second cylindrical portion 136 including the protrusions 136a may be integrally formed using a mold. The protrusions 136a only have to fix the positional relationship between the first cylindrical portion 134 and the second cylindrical portion 136. The number of protrusions 136a is not limited to three and may be two, four, or more. For facilitation of stable fixing between the first cylindrical portion 134 and the second cylindrical portion 136, three or more protrusions 136a are preferable.

The inner protective cover 130 defines an element-chamber inlet 127 (see FIGS. 3 to 5), which is a gap between the first member 131 and the second member 135 and serves as an inlet for the measurement target gas into the sensor element chamber 124. More specifically, the element-chamber inlet 127 is formed as a cylindrical gap or a gas flow path between the external circumferential surface of the first cylindrical portion 134 and the internal circumferential surface of the second cylindrical portion 136. The element-chamber inlet 127 includes an outer opening 128, which is an opening facing the first gas chamber 122 in which outer inlets 144a are disposed, and an element-side opening 129, which is an opening facing the sensor element chamber 124 in which the gas inlet 111 is disposed. The outer opening 128 is formed closer to the rear end of the sensor element 110, upper in FIG. 3, than the element-side opening 129. Thus, the element-chamber inlet 127 serves as a flow path for the measurement target gas from the rear end, or the upper end in FIG. 3, to the front end, or the lower end in FIG. 3, of the sensor element 110 in the course of the measurement target gas while it flows from the outer inlets 144a to the gas inlet 111. The element-chamber inlet 127 serves as a flow path parallel to the direction connecting the rear end and the front end of the sensor element 110, that is, a vertical flow path in FIG. 3.

The element-side opening 129 is formed at a position spaced apart from the gas inlet 111 the distance A1 (see FIG. 4) −1.5 mm or more. The distance A1 may 0 mm or more or may exceed 1.5 mm. The distance A1 is a distance extending in a direction connecting the rear end and the front end of the sensor element 110, that is, the vertical direction in FIG. 3, where the direction from the front end to the rear end, that is, the upward direction in FIG. 3 is regarded as a positive direction. The distance A1 is a distance in a direction connecting the rear end and the front end of the sensor element 110 and between a portion of the opening end portion of the gas inlet 111 closest to the element-side opening 129 and a portion of the end portion of the element-side opening 129 closest to the gas inlet 111. In FIG. 3, in the case where the gas inlet is a horizontal hole open in the side surface of the sensor element 110 and the element-side opening 129 is positioned between the upper end and the lower end of the opening of the gas inlet, the distance A1 is regarded as 0 mm. The upper limit of the distance A1 is determined in accordance with the shape of the inner protective cover 130 or the sensor element chamber 124. The distance A1 may be 7.5 mm or less, but is not limited to these values.

The element-side opening 129 is formed at a position spaced apart from the gas inlet 111 a distance A2 (see FIG. 4). The distance A2 is a distance in a direction perpendicular to the direction connecting the front end and the rear end of the sensor element 110. The distance A2 is a distance in the direction perpendicular to the direction connecting the rear end and the front end of the sensor element 110 and between a portion of the opening end portion of the gas inlet 111 closest to the element-side opening 129 and a portion of the end portion of the element-side opening 129 closest to the gas inlet 111. The sensor element 110 and the element-side opening 129 become further separated from each other with increasing distance A2, whereby the effect of preventing the sensor element 110 from being cooled tends to be enhanced. For example, the distance A2 may fall within the range of 0.6 mm to 3.0 mm although the distance A2 is not limited to these values. The element-side opening 129 is open in the direction from the rear end to the front end of the sensor element 110 and parallel to the direction connecting the rear end and the front end of the sensor element 110. Specifically, the element-side opening 129 is open downward that is, directly downward in FIG. 3. Thus, the sensor element 110 is disposed in a region other than the region formed by imaginarily extending the element-chamber inlet 127 from the element-side opening 129, that is, the region immediately below the element-side opening 129 in FIG. 3. This configuration can prevent the measurement target gas that has flowed out of the element-side opening 129 from directly coming into contact with the surface of the sensor element 110, whereby the sensor element 110 can be prevented from being cooled.

The outer opening 128 is formed at a position spaced apart from the outer inlets 144a a distance A3 (see FIG. 4). The distance A3 is a distance extending in a direction connecting the front end and the rear end of the sensor element 110, that is, the vertical direction in FIG. 3, and the direction from the front end to the rear end is regarded as a positive direction as in the case of the distance A1. The distance A3 is a distance extending in a direction connecting the rear end and the front end of the sensor element 110 and between a portion of the opening end portion of the outer inlets 144a closest to the outer opening 128 and a portion of the end portion of the outer opening 128 closest to the outer inlets 144a. In this embodiment, the outer inlets 144a include horizontal holes 144b and vertical holes 144c. The portion of the outer inlets 144a closest to the element-side opening 129 in the vertical direction in FIG. 3 is an upper end of the horizontal holes 144b. Thus, as illustrated in FIG. 4, the distance between the upper end of the horizontal hole 144b and the outer opening 128 is regarded as the distance A3. For example, when the outer opening 128 is positioned lower than the lower end of the vertical holes 144c in the vertical direction in FIG. 3, the distance between the lower end of the vertical holes 144c and the outer opening 128 in the vertical direction is regarded as the distance A3. The outer opening 128 may be formed at a position at which the distance A3 takes a positive value or a negative value. Nevertheless, the distance A3 is preferably 0 or more. In other words, the outer opening 128 is preferably disposed at a position closer to the rear end of the sensor element, or upper in FIG. 3, than at least one of the outer inlets 144a. Specifically, in this embodiment, the outer opening 128 is preferably disposed at the position the same as or higher than the lower end, that is, the undersurface of a stepped portion 143b, of the vertical holes 144c.

The external circumferential surface of the first cylindrical portion 134 and the internal circumferential surface of the second cylindrical portion 136 are separated from each other by a distance A4 in the radial direction of the cylinder at the element-side opening 129 and by a distance A5 in the radial direction of the cylinder at the outer opening 128. In addition, the external circumferential surface of the first cylindrical portion 134 and the internal circumferential surface of the second cylindrical portion 136 are separated from each other by a distance A7 at a position at which the protrusions 136a and the first cylindrical portion 134 touch each other (see the cross section illustrated in FIG. 5). For example, the distance A4, the distance A5, and the distance A7 may fall within the range of 0.3 mm to 2.4 mm, although each distance is not limited to these values. By adjusting the value of the distance A4 or the distance A5, the opening area of the element-side opening 129 or the opening area of the outer opening 128 can be adjusted. In this embodiment, the distance A4, the distance A5, and the distance A7 are assumed to be equal to one another and the opening area of the element-side opening 129 and the opening area of the outer opening 128 are assumed to be equal to each other. In this embodiment, the distance A4 (and the distance A5 and the distance A7) is equal to half of the difference between the outer diameter of the first cylindrical portion 134 and the inner diameter of the second cylindrical portion 136. For example, the distance between the element-side opening 129 and the outer opening 128 in the vertical direction, that is, the vertical distance L of the element-chamber inlet 127, which is equivalent to the path length of the element-chamber inlet 127, may be greater than 0 mm and 6.6 mm or less, although the distance is not particularly limited to these values.

When the shortest distance from the surface of the sensor element 110 to the protective cover 120 is determined as a distance A6 (see FIG. 4), the effect of preventing the sensor element 110 from being cooled tends to be enhanced with increasing distance A6. This is because the heat from the heater of the sensor element 110 is more likely to be absorbed by the protective cover 120 with decreasing distance A6, that is, decreasing distance between the sensor element 110 and the protective cover 120. In this embodiment, a portion of the protective cover 120 closest to the sensor element 110 is the internal circumferential surface of the first cylindrical portion 134 of the inner protective cover 130. Thus, as illustrated in FIG. 4, the distance A6 is a distance between the side surface of the sensor element 110 and the internal circumferential surface of the first cylindrical portion 134 in the radial direction or the lateral direction in FIG. 4. Here, the distance A6 is the shortest distance between the sensor element 110 and the protective cover 120. Thus, depending on the shape of the protective cover, the distance A6 may be, for example, a distance between the sensor element 110 and the protective cover in the axial direction or the vertical direction in FIG. 4. In this manner, the distance A6 is not limited to the distance in the lateral direction in FIG. 4. For example, the distance A6 may fall within the range of 0.6 mm to 3.0 mm, although the distance A6 is not particularly limited to these values. The heat from the heater is more likely to be absorbed by the protective cover 120 with increasing thickness of the protective cover 120, that is, increasing heat capacity of the protective cover 120. In this embodiment, the inner protective cover 130 is located close to the sensor element 110. Thus, the heat from the heater is more likely to be absorbed by the protective cover 120 with increasing thickness of the inner protective cover 130. Thus, the heat retaining property of the sensor element 110 is more likely to be enhanced with increasing distance A6 or decreasing thickness of the protective cover 120, particularly, the inner protective cover 130.

As illustrated in FIG. 3, the outer protective cover 140 includes a cylindrical large-diameter portion 142, a cylindrical barrel 143, which is connected to the large-diameter portion 142 and has a smaller diameter than the large-diameter portion 142, and the bottomed cylindrical front end portion 146, which has a smaller inner diameter than the barrel 143. The barrel 143 has a side portion 143a, which has a side surface extending in the center axis direction, or the vertical direction in FIG. 3, of the outer protective cover 140, and the stepped portion 143b, which is a bottom portion of the barrel 143 and connects the side portion 143a and the front end portion 146 together. The center axes of the large-diameter portion 142, the barrel 143, and the front end portion 146 are coaxial with the center axis of the inner protective cover 130. The large-diameter portion 142 has its internal circumferential surface abutting the housing 102 and the large-diameter portion 132, so that the outer protective cover 140 is fixed to the housing 102. The barrel 143 is positioned so as to cover the outer peripheries of the first cylindrical portion 134 and the second cylindrical portion 136. The front end portion 146 is positioned so as to cover the front end portion 138 and has its internal circumferential surface abutting the external circumferential surface of the connection portion 137. The outer protective cover 140 includes multiple outer inlets 144a, twelve in this embodiment, formed in the barrel 143 and serving as inlets for the measurement target gas from the outside, and multiple outer outlets 147a, six in this embodiment, formed in the front end portion 146 and serving as outlets for the measurement target gas to the outside.

The outer inlets 144a are holes communicating with the outer side or outside of the outer protective cover 140 and the first gas chamber 122 and these holes are also referred to as first outer gas holes. The outer inlets 144a include multiple horizontal holes 144b, six in this embodiment, equidistantly formed in the side portion 143a and multiple vertical holes 144c, six in this embodiment, equidistantly formed in the stepped portion 143b (see FIGS. 3, 5, and 6). These outer inlets 144a, that is, the horizontal holes 144b and the vertical holes 144c are circular or perfectly circular holes. The diameter of these twelve outer inlets 144a is not limited to a particular value and may fall within the range of 0.5 mm to 1.5 mm, for example. In this embodiment, the multiple outer inlets 144a have the same diameter. As illustrated in FIG. 5, the outer inlets 144a are formed in such a manner that the horizontal holes 144b and the vertical holes 144c are alternately arranged at equal intervals when viewed in the circumferential direction of the outer protective cover 140. Specifically, an angle between the line connecting the center of one horizontal hole 144b in FIG. 5 to the center axis of the outer protective cover 140 and the line connecting the center of the vertical hole 144c adjacent to the horizontal hole 144b to the center axis of the outer protective cover 140 is 30° (360°/12).

The outer outlets 147a are holes communicating with the outer side or outside of the outer protective cover 140 and the second gas chamber 126 and these holes are also referred to as second outer gas holes. The outer outlets 147a include multiple horizontal holes 147b, three in this embodiment, equidistantly formed in the side portion of the front end portion 146, and multiple vertical holes 147c, three in this embodiment, equidistantly formed in the bottom portion of the front end portion 146 in the circumferential direction of the outer protective cover 140 (see FIGS. 3 and 6). These outer outlets 147a, that is, the horizontal holes 147b and the vertical holes 147c are circular or perfectly circular holes. The diameter of these six outer outlets 147a is not limited to a particular value and may fall within the range of 0.5 mm to 2.0 mm, for example. In this embodiment, the multiple outer outlets 147a all have the same diameter. As in the case of the outer inlets 144a, the outer outlets 147a are formed in such a manner that the horizontal holes 147b and the vertical holes 147c are alternately arranged at equal intervals when viewed in the circumferential direction of the outer protective cover 140. Specifically, when viewed in a cross section taken perpendicular to the center axis of the outer protective cover 140, an angle between the line connecting the center of one horizontal hole 147b to the center axis of the outer protective cover 140 and the line connecting the center of the vertical hole 144c adjacent to the horizontal hole 144b to the center axis of the outer protective cover 140 is 60° (360°/6).

The first gas chamber 122 is a space surrounded by the stepped portion 133, the first cylindrical portion 134, the second cylindrical portion 136, the large-diameter portion 142, the side portion 143a, and the stepped portion 143b. The sensor element chamber 124 is a space surrounded by the inner protective cover 130. The second gas chamber 126 is a space surrounded by the front end portion 138 and the front end portion 146. Here, the internal circumferential surface of the front end portion 146 abuts the external circumferential surface of the connection portion 137. Thus, the first gas chamber 122 and the second gas chamber 126 do not communicate with each other. The outer bottom surface of the front end portion 138 and the inner bottom surface of the front end portion 146 are separated from each other by a distance B2. The space or the capacity of the second gas chamber 126 increases with increasing distance B2. For example, the distance B2 may fall within the range of 1.9 mm to 9.0 mm, although the distance B2 is not particularly limited to these values.

Here, the flow of the measurement target gas in the protective cover 120 of the gas sensor 100 is described. The measurement target gas that flows in the pipe 20 firstly passes through any of the multiple outer inlets 144a that is, the horizontal holes 144b and the vertical holes 144c and flows into the first gas chamber 122. Subsequently, the measurement target gas flows from the first gas chamber 122 into the element-chamber inlet 127 through the outer opening 128. Then, the measurement target gas flows out from the element-chamber inlet 127 through the element-side opening 129 and flows into the sensor element chamber 124. Here, the gas flow path from the outside to the sensor element chamber 124 including the element-chamber inlet 127, that is, the gas flow path including the outer inlets 144a, the first gas chamber 122, and the element-chamber inlet 127 is referred to as an inlet-side gas flow path 150 (see the hatched portion in FIG. 7). At least part of the measurement target gas that has flowed into the sensor element chamber 124 from the element-side opening 129 arrives at the gas inlet 111 of the sensor element 110. At this time, the shortest flow path in the sensor element chamber 124 for the measurement target gas from the element-chamber inlet 127 or the element-side opening 129 to the gas inlet 111 is referred to as an in-element-chamber flow path 152 (see the hatched portion in FIG. 7). As illustrated in FIG. 7, the upper end of the in-element-chamber flow path 152 and the element-side opening 129 are vertically positioned at the same position and the lower end of the in-element-chamber flow path 152 and the gas inlet 111 are vertically positioned at the same position. In this manner, the in-element-chamber flow path 152 is determined without considering the thickness of the porous protective layer 110a. Thus, in this embodiment, the vertical dimension of the in-element-chamber flow path 152 is equal to the distance A1.

The measurement target gas in the sensor element chamber 124 flows through the element-chamber outlet 138a into the second gas chamber 126 and flows out to the outside through any of the multiple outer outlets 147a. Here, the gas flow path including the element-chamber outlet 138a from the sensor element chamber 124 to the outside, that is, the gas flows path including the element-chamber outlet 138a, the second gas chamber 126, and the outer outlets 147a is referred to as an outlet-side gas flow path 154 (see the hatched portion in FIG. 7).

Here, the size, the shape, and other parameters of the protective cover 120 are adjusted in such a manner that a gas-contact surface area S falls within the range of 450 mm$^2$ to 1145 mm$^2$, where the gas-contact surface area S is the sum of a surface area S1 of a portion facing the inlet-side gas flow path 150 and a surface area S2 of a portion facing the in-element-chamber flow path 152. In FIG. 7, portions of the protective cover 120 facing the inlet-side gas flow path 150 and portions of the protective cover 120 facing the in-element-chamber flow path 152 are drawn with solid lines and other portions are drawn with broken lines. As is clear from FIG. 7, the surface area S1 is the sum of the areas of the internal circumferential surfaces of the outer inlets 144a that is, the horizontal holes 144b and the vertical holes 144c, the areas of portions of the large-diameter portion 142, the barrel 143, the first member 131, and the second member 135 exposed to the inside of the first gas chamber 122, and the areas of portions of the first member 131 and the second member 135 exposed to the inside of the element-chamber inlet 127. The surface area S2 is the sum of the areas of portions of the first member 131 and the second member 135 exposed to the inside of the in-element-chamber flow path 152. More specifically, the surface area S2 is the sum of the area of the lower end surface of the first cylindrical portion 134 and the areas of portions of the second cylindrical portion 136 and the connection portion 137 exposed to the inside of the in-element-chamber flow path 152. The gas-contact surface area S is a value relating to the size of the surface area of the protective cover 120 that the measurement target gas touches from when it flows into the protective cover 120 and until when it arrives at the gas inlet 111.

The gas sensor 100 preferably has the shape, the size, the number, or other properties of the element-chamber inlet 127, the element-chamber outlet 138a, the outer inlets 144a, and the outer outlets 147a adjusted in such a manner that the area ratio α falls within the range of 12 to 35. The area ratio α is equal to the cross-sectional area G2×the cross-sectional area G3×the cross-sectional area G4/the cross-sectional area G1. The cross-sectional area G1 [mm$^2$] is the sum of the cross-sectional areas of the outer inlets 144a taken perpendicularly to the flow of the measurement target gas. In this embodiment, the twelve outer inlets 144a, the horizontal holes 144b and the vertical holes 144c, have the same diameter. When the radius of each outer inlet 144a is denoted by r1, the cross-sectional area G1 is equal to (π×radius r1×radius r1)×12. The cross-sectional area G2 [mm$^2$] is a cross-sectional area of the element-chamber inlet 127 taken perpendicularly to the flow of the measurement target gas. In this embodiment, the protrusions 136a are formed. Thus, the cross-sectional area of the element-chamber inlet 127 taken perpendicularly to the flow of the measurement target gas is not uniform, that is, the element-chamber inlet 127 has portions at which the cross-sectional area changes in the direction of the flow of the measurement target gas. In this case, the cross-sectional area G2 is determined as the smallest cross-sectional area of the element-chamber inlet 127. For example, in the element-chamber inlet 127, the cross-sectional area of a portion at which the protrusions 136a and the first cylindrical portion 134 touch each other taken perpendicularly to the flow of the measurement target gas, or the area of cross section of the element-chamber inlet 127 illustrated in FIG. 5, is smaller than the cross-sectional area at the element-side opening 129 taken perpendicularly to the flow of the measurement target gas, whereby the former cross-sectional area is determined as the smallest cross-sectional area. Thus, the area of cross section of the element-chamber inlet 127 illustrated in FIG. 5 is determined as the cross-sectional area G2. The cross-sectional area G3 [mm$^2$] is the cross-sectional area at the element-chamber outlet 138a taken perpendicularly to the flow of the measurement target gas. In this embodiment, when the radius of the element-chamber outlet 138a is denoted by r3, the cross-sectional area G3 is equal to (π×radius r3×radius r3). The cross-sectional area G4 [mm$^2$] is the sum of the cross-sectional areas of the outer outlets 147a taken perpendicularly to the flow of the measurement target gas. In this embodiment, the six outer outlets 147a, the horizontal holes 147b and the vertical holes 147c, have the same diameter. When the radius is denoted by r4, the cross-sectional area G4 is equal to (π×radius r4×radius r4)×6. The area ratio α thus obtained increases with decreasing cross-sectional area G1, representing the size of the inlet into the protective cover 120 from the outside. The area ratio α increases with increasing cross-sectional area G2 or G3, representing the size of the inlet or the outlet of the sensor element chamber 124 that determines the flow rate of the measurement target gas in the protective cover 120, or with increasing cross-sectional area G4, representing the size of the outlet from the inside of the protective cover 120 to the outside. Thus, the area ratio α represents how smoothly the measurement target gas that flows into the protective cover 120 flows, or the flow rate of the measurement target gas. Although not particularly limited to these, for example, the cross-sectional area G1 may fall within the range of 4 to 15 mm$^2$, the cross-sectional area G2 may fall within the range of 2 to 35 mm$^2$, the cross-sectional area G3 may fall within the range of 0.5 to 5 mm$^2$, and the cross-sectional area G4 may fall within the range of 2.5 to 7.5 mm$^2$. The area ratio α is more preferably 18 or more. The cross-sectional area G2 may be 40 mm$^2$ or less.

In this embodiment, one element-chamber inlet 127 is provided. In the case, however, where multiple element-chamber inlets are provided, as in the case of the cross-sectional area G1 or G4, the sum of the cross-sectional areas of the element-chamber inlets is determined as the cross-sectional area G2. The same holds true for the cross-sectional area G3. In this embodiment, each outer inlet 144a has a uniform cross-sectional area taken perpendicularly to the flow of the measurement target gas, that is, the cross-sectional area does not change in the direction of the flow of the measurement target gas. In the case, however, where the cross-sectional area is not uniform, as in the case of the cross-sectional area G2, the sum of the smallest cross-sectional areas of the outer inlets is determined as the cross-sectional area G1. The same holds true for the cross-sectional area G3 or G4.

Subsequently, ammonia concentration detection performed by the gas sensor 100 having this configuration is described. As described above, when the measurement target gas passes through the inlet-side gas flow path 150 and the sensor element chamber 124 and flows into the sensor element 110 through the gas inlet 111, the sensor element 110 converts ammonia in the measurement target gas into NOx and produces an electric signal, such as voltage or electric current, corresponding to the concentration of the converted NOx. On the basis of this electric signal, the engine ECU 6 detects the ammonia concentration in the measurement target gas. In addition, an output of the heater in the sensor element 110 is controlled by, for example, the engine ECU 6 so that a predetermined temperature is maintained. Here, the measurement target gas before flowing into the gas sensor 100 does not contain NOx since the measurement target gas is detoxified after NOx is reduced by the SCR catalyst 5. However, the measurement target gas contains an excessive amount of ammonia. When the ammonia is oxidized in the sensor element 110 and converted into NOx, NOx derived from ammonia occurs. Thus, measuring the NOx concentration enables detection of the ammonia concentration in the measurement target gas.

Here, as described above, the protective cover 120 contains at least one of chromium or nickel, which has a capability of decomposing ammonia. Thus, while the measurement target gas passes through the inlet-side gas flow path 150 and the sensor element chamber 124, ammonia (NH$_3$) in the measurement target gas that has touched the protective cover 120 may be decomposed into nitrogen (N$_2$) or NOx and hydrogen (H$_2$) or water (H$_2$O). When ammonia is decomposed by the protective cover 120 in this manner, the ammonia concentration in the measurement target gas changes before the measurement target gas arrives at the gas inlet 111, whereby the accuracy of the ammonia concentration detection is lowered. In the gas sensor 100 according to the embodiment, however, the gas-contact surface area S is 1145 mm$^2$ or less, so that the area of the protective cover 120 that the measurement target gas touches from when it passes through the protective cover 120 until when it arrives at the gas inlet 111 is reduced to a sufficiently small level. This configuration can thus prevent ammonia in the measurement target gas from being decomposed by the protective cover 120, whereby the accuracy of the ammonia concentration detection can be prevented from being lowered. In the case where the gas-contact surface area S is 450 mm$^2$ or more, failures resulting from simplifying the path for the measurement target gas, that is, the inlet-side gas flow path 150 and the in-element-chamber flow path 152, from when it passes through the protective cover 120 until it arrives at the gas inlet 111 can be prevented. Examples of failures resulting from simplifying the path for the measurement target gas include facilitation of arrival of external poisoned substances to the sensor element 110 or cracking resulting from facilitation of adhesion of moisture in the measurement target gas to the sensor element 110. As the gas-contact surface area S is decreasing, the effect of suppressing decomposition of ammonia in the measurement target gas by the protective cover 120 is enhanced. In this respect, the gas-contact surface area S may be, for example, 1100 mm$^2$ or less, 1050 mm$^2$ or less, 1040 mm$^2$ or less, 1000 mm$^2$ or less, 950 mm$^2$ or less, 900 mm$^2$ or less, 850 mm$^2$ or less, or 800 mm$^2$ or less. As the gas-contact surface area S is increasing, failures resulting from simplifying the path for the measurement target gas are more likely to be suppressed. In this respect, the gas-contact surface area S is preferably, for example, 500 mm$^2$ or more, 550 mm$^2$ or more, 600 mm$^2$ or more, 650 mm$^2$ or more, and may be 700 mm$^2$ or more or 750 mm$^2$ or more.

According to the embodiment described in detail thus far, ammonia in the measurement target gas can be prevented from being decomposed by the protective cover 120 by making the gas-contact surface area S 1145 mm$^2$ or less. When the gas-contact surface area S is 450 mm$^2$ or more, failures resulting from simplifying the path for the measurement target gas from when it passes through the protective cover 120 until it arrives at the gas inlet 111 of the sensor element 110 can be prevented.

In the protective cover 120, the element-chamber inlet 127 is formed at the position spaced apart from the gas inlet 111 a distance A1 that is −1.5 mm or more and the element-chamber outlet 138a is formed at the position located away from the gas inlet 111 in the direction toward the front end from the rear end, or the lower direction in FIG. 3, of the sensor element 110. Here, the element-chamber outlet 138a is located away from the gas inlet 111 in the direction toward the front end from the rear end of the sensor element 110, that is, the distance B1 is less than 0 mm. In the case where the distance A1 is less than −1.5 mm, the measurement target gas is less likely to flow smoothly and more likely to stagnate around the gas inlet 111 in the sensor element chamber 124. When the measurement target gas stagnates, the time period for which the measurement target gas and the protective cover 120 touch each other increases, whereby ammonia in the measurement target gas is more likely to be decomposed. When the distance A1 is −1.5 mm or more, the measurement target gas is more likely to flow smoothly, whereby ammonia in the measurement target gas can be prevented from being decomposed by the protective cover 120.

The protective cover 120 also includes the inner protective cover 130 and the outer protective cover 140 that define the outlet-side gas flow path 154 including one element-chamber outlet 138a. The outer protective cover 140 is disposed on the outer side of the inner protective cover 130. The inner protective cover 130 defines the sensor element chamber 124, the element-chamber inlet 127, and the element-chamber outlet 138a. The outer protective cover 140 defines the multiple outer inlets 144a, constituting part of the inlet-side gas flow path 150, and the multiple outer outlets 147a, constituting part of the outlet-side gas flow path 154. The outer protective cover 140 and the inner protective cover 130 define the first gas chamber 122 as a space between themselves. The first gas chamber 122 is part of the inlet-side gas flow path 150 and located between the outer inlets 144a and the element-chamber inlet 127. The outer protective cover 140 and the inner protective cover 130 define the second gas chamber 126 as a space between themselves. The second gas chamber 126 is part of the outlet-side gas flow path 154 and located between the outer outlets 147a and the element-chamber outlet 138a. The second gas chamber 126 does not directly communicate with the first gas chamber 122.

Furthermore, the inner protective cover 130 defines the element-chamber outlet 138a located away from the element-chamber inlet 127 in the direction toward the front end from the rear end of the sensor element 110. The outer protective cover 140 includes the cylindrical barrel 143, in which the outer inlets 144a are formed, and the bottomed cylindrical front end portion 146, which has a smaller inner diameter than the barrel 143 and in which the outer outlets 147a located away from the outer inlets 144a in the direction toward the front end from the rear end of the sensor element 110 are formed. The outer protective cover 140 and the inner protective cover 130 define the first gas chamber 122 between the barrel 143 and the inner protective cover 130 and define the second gas chamber 126 between the front end portion 146 and the inner protective cover 130.

The area ratio α falls within the range of 12 to 35. As the area ratio α increases, the cross-sectional areas G2, G3, and G4 of the element-chamber inlet 127, the element-chamber outlet 138a, and the outer outlets 147a increase with respect to the cross-sectional areas G1 of the respective outer inlets 144a, whereby the measurement target gas is more likely to flow smoothly through the protective cover 120. In the case where the area ratio α is 12 or more, the measurement target gas flows very smoothly in the protective cover 120 so that the time period for which the measurement target gas touches the protective cover 120 until it arrives at the gas inlet 111 of the sensor element 110 is shortened. Thus, ammonia in the measurement target gas can be prevented from being decomposed by the protective cover 120 and the accuracy of ammonia concentration detection can be prevented from being lowered. In the case where the area ratio α is 35 or less, cooling of the sensor element 110 due to an excessively high flow rate of the measurement target gas can be prevented, whereby cracking of the sensor element 110 can be prevented. As the area ratio α is increasing, the effect of suppressing decomposition of ammonia in the measurement target gas by the protective cover 120 is enhanced. In this respect, the area ratio α is, for example, preferably 12.79 or more, more preferably 13 or more, still more preferably 18 or more. As the area ratio α is decreasing, the effect of suppressing the cooling of the sensor element 110 is enhanced. In this respect, the area ratio α is, for example, preferably 34.20 or less, more preferably 30 or less, still more preferably 27 or less, further still more preferably 24 or less, and may be 20 or less or 19.70 or less.

In the protective cover 120, the element-chamber inlet 127 is formed in such a manner that the element-side opening 129 of the element-chamber inlet 127, which is an opening facing the sensor element chamber 124, is open in a direction from the rear end to the front end of the sensor element 110, that is, open downward in FIG. 3. This configuration can prevent the measurement target gas that has flowed out of the element-side opening 129 from perpendicularly coming into contact with the surface of the sensor element 110, that is, a portion of the surface other than the gas inlet 111, or from arriving at the gas inlet 111 after flowing a long distance over the surface of the sensor element 110. Cooling of the sensor element 110 can thus be prevented. Since cooling of the sensor element 110 is prevented by adjusting the orientation of the opening of the element-side opening 129 instead of reducing the flow rate or the flow speed of the measurement target gas, the responsivity to the gas concentration detection can be prevented from being lowered. These features make the responsivity and the heat retaining property of the sensor element 110 compatible. Moreover, since the element-side opening 129 is open parallel to the direction connecting the rear end and the front end of the sensor element 110, the measurement target gas that has flowed out of the element-side opening 129 can be prevented from directly coming into contact with the surface of the sensor element 110, whereby cooling of the sensor element 110 can be further securely prevented.

The protective cover 120 is formed of a metal containing at least one of chromium or nickel as a substance having a capability of decomposing ammonia. Since the protective cover 120 contains at least one of chromium or nickel, the protective cover 120 can have a higher corrosion resistance.

It should be understood that the present invention is not limited to the embodiments described above and may be embodied in various modes within the technical scope of the invention.

Figure 8:
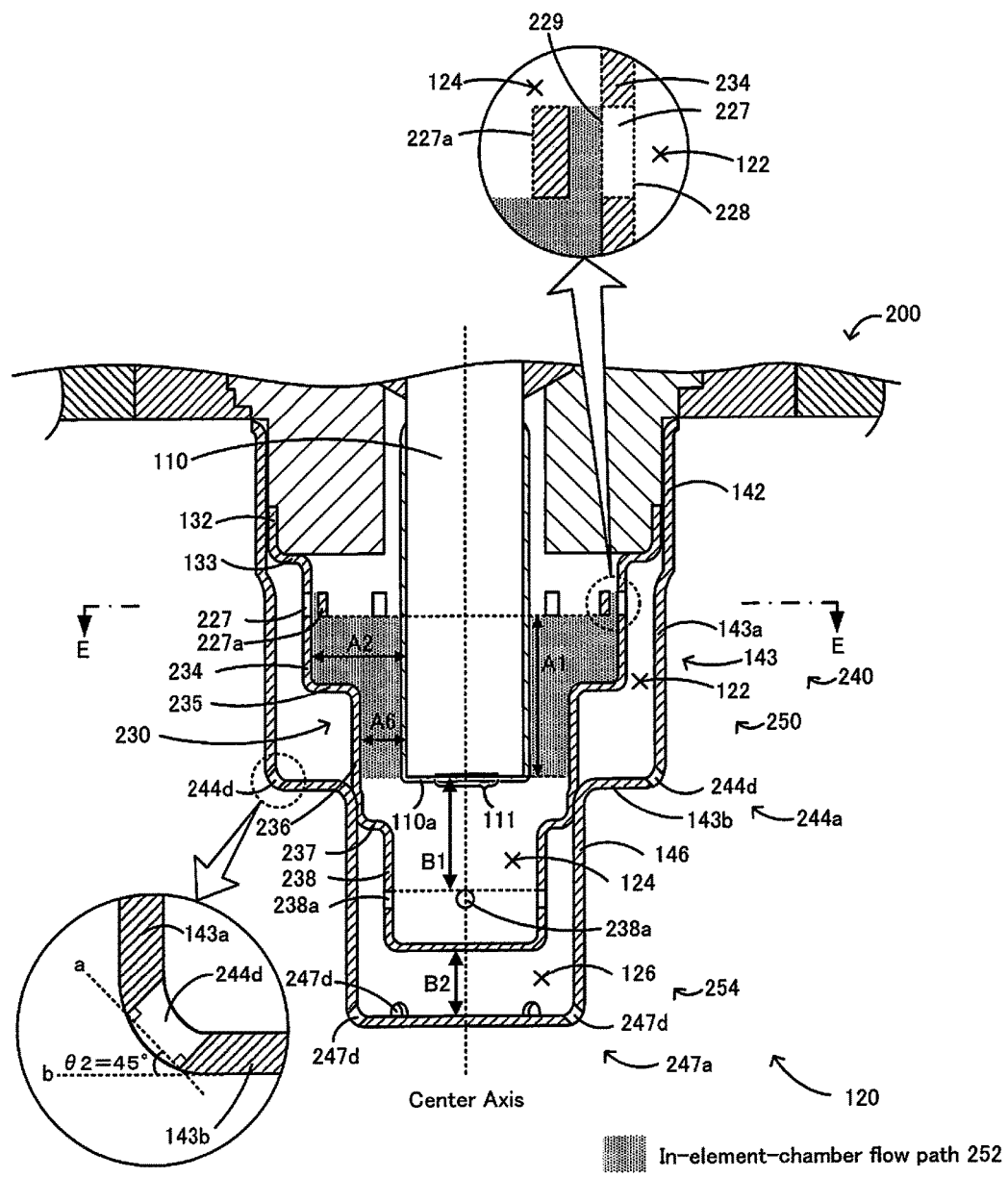
FIG. 8 is a vertical sectional view of a gas sensor 200 according to a modified example.
Figure 9:
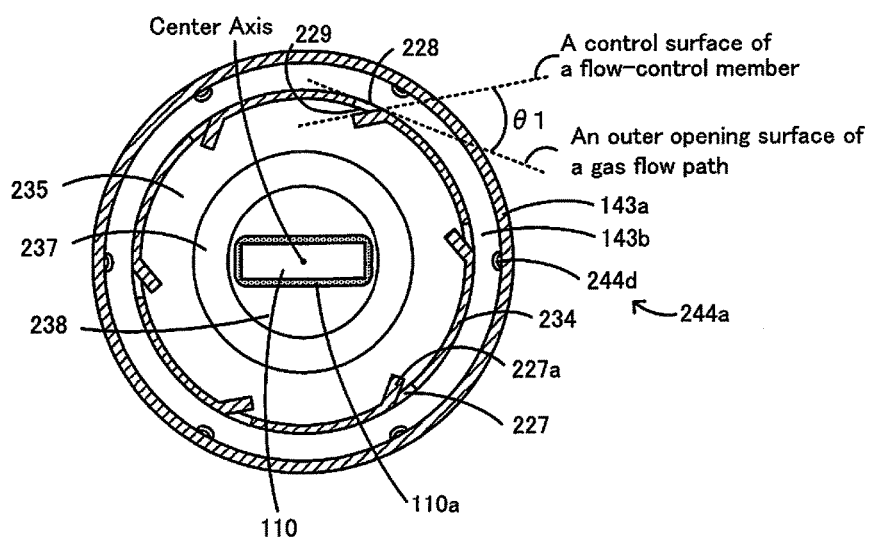
FIG. 9 is a cross-sectional view taken along the line E-E of FIG. 8.

For example, the shape of the protective cover 120 is not limited to the one described in the above-described embodiment. FIG. 8 is a vertical sectional view of a gas sensor 200 according to a modified example. FIG. 9 is a cross-sectional view taken along the line E-E of FIG. 8. In FIG. 8 and FIG. 9, components that are the same as those of the gas sensor 100 are denoted by the same symbols and not described in detail. As illustrated in FIGS. 8 and 9, the gas sensor 200 includes an inner protective cover 230 instead of the inner protective cover 130. The inner protective cover 230 is formed of one member and includes a large-diameter portion 132, a cylindrical first barrel 234 having a smaller diameter than the large-diameter portion 132, a cylindrical second barrel 236 having a smaller diameter than the first barrel 234, and a bottomed cylindrical front end portion 238 having a smaller diameter than the second barrel 236. The large-diameter portion 132 and the first barrel 234 are connected together by a stepped portion 133. The inner protective cover 230 also includes a stepped portion 235, which connects the first barrel 234 and the second barrel 236 together, and a stepped portion 237, which connects the second barrel 236 and the front end portion 238 together. The large-diameter portion 132, the first barrel 234, the second barrel 236, and the front end portion 238 have a common center axis. The first barrel 234 and the second barrel 236 are disposed so as to cover the side surface of the sensor element 110. In the first barrel 234, element-chamber inlets 227, which are multiple rectangular through holes, or horizontal holes, six holes in the gas sensor 200, and plate-shaped flow-control members 227a, which control the flow of the measurement target gas that flows into the sensor element chamber 124 through the element-chamber inlets 227, are formed. As illustrated in FIG. 9, the element-chamber inlets 227 are equidistantly formed along the outer circumference of the first barrel 234. The element-chamber inlets 227 also are formed as gas flow paths in a direction perpendicular to the direction connecting the front end and the rear end of the sensor element 110. The element-chamber inlets 227 are formed as gas flow paths in a direction toward the center axis, or in the radial direction, when viewed in a cross section taken perpendicularly to the center axis of the first barrel 234. An opening of each element-chamber inlet 227 located on the outer side of the first barrel 234 is determined as an outer opening 228 and an opening of each element-chamber inlet 227 located on the inner side of the first barrel 234 is determined as an element-side opening 229. As illustrated in FIG. 9, the flow-control members 227a correspond one to one to the multiple element-chamber inlets 227. Each flow-control member 227a is disposed so as to be positioned between the corresponding element-chamber inlet 227 and the sensor element 110. The multiple flow-control members 227a are formed so as to be rotationally symmetric, that is, six-fold rotationally symmetric in this embodiment. An angle θ1, see FIG. 9, between a control surface of each flow-control member 227a and an outer opening surface of the corresponding element-chamber inlet 227 is fixed at such an angle that the measurement target gas that passes through the element-side opening 229 of the element-chamber inlet 227 is prevented from directly flowing toward the sensor element 110. This configuration prevents the measurement target gas that has flowed out of the element-side opening 229 from directly coming into contact with the surface of the sensor element 110, whereby cooling of the sensor element 110 can be prevented. For example, the angle θ1 may fall within the range of 20° to 70° or within the range of 25° to 67.5°. In the side surface of the front end portion 238, four element-chamber outlets 238a, which are holes communicating with the sensor element chamber 124 and the second gas chamber 126, are equidistantly formed.

An outer protective cover 240 has the same configuration as the outer protective cover 140 except that it has outer inlets 244a and outer outlets 247a instead of the outer inlets 144a and the outer outlets 147a. The outer inlets 244a include multiple corner holes 244d, six in the gas sensor 200, instead of including the horizontal holes 144b and the vertical holes 144c. The corner holes 244d are formed at corner portions on the boundary of the side portion 143a and the stepped portion 143b. An angle θ2 between an outer opening surface of each corner hole 244d, or the line a in an enlarged view in the lower left of FIG. 8, and a bottom surface or an undersurface of the stepped portion 143b, or the line b in the enlarged view in the lower left of FIG. 8, falls within the range of 10° to 80°, or 45° in FIG. 8. As in the case of the outer inlets 244a, the outer outlets 247a include multiple corner holes 247d, six in the gas sensor 200. The corner holes 247d are formed at corner portions on the boundary of the side portion and the bottom portion of the front end portion 146. The inclination of the corner holes 247d is 45° as in the angle θ2 of the corner holes 244d. As illustrated in FIG. 8, the distance A1 in the gas sensor 200 according to the modified example is a distance from the gas inlet 111 to the lower end of the element-side opening 229 in the vertical direction. Similarly, the distance A2 is a distance from the end portion, or the left end in FIG. 8, of the sensor element 110 to the element-side opening 229 in the lateral direction. The distance A6 is a shortest distance between the sensor element 110 to the internal circumferential surface of the second barrel 236. The protective cover 120 defines an inlet-side gas flow path 250 constituted by the outer inlets 244a, the first gas chamber 122, and the element-chamber inlets 227. The sum of the areas of portions of the inner protective cover 230 and the outer protective cover 240 facing the inlet-side gas flow path 250 is determined as the surface area S1. The shortest flow path in the sensor element chamber 124 for the measurement target gas from the upper end of the element-chamber inlets 227, or the element-side openings 229, to the gas inlet 111 is determined as an in-element-chamber flow path 252 (see the hatched portion in FIG. 8). The sum of the areas of portions of the inner protective cover 230 facing the in-element-chamber flow path 252 is determined as the surface area S2. In the enlarged view in the upper right of FIG. 8, portions of the inner protective cover 230 facing the in-element-chamber flow path 252 are drawn with solid lines and other portions are drawn with broken lines. As is clear from the enlarged view in the upper right of FIG. 8, the surface area S2 includes the area of the surface, that is, the control surface, of the flow-control member 227a facing the element-chamber inlet 227 and the area of the undersurface of the flow-control member 227a. The protective cover 120 defines an outlet-side gas flow path 254 constituted by the element-chamber outlets 238a, the second gas chamber 126, and the outer outlets 247a. The gas sensor 200 having the above-described configuration can also attain the same effects since it has the similar features to the above-described embodiment. For example, when the gas-contact surface area S is determined to fall within the range of 450 mm$^2$ to 1145 mm$^2$, the failures resulting from simplifying the path for the measurement target gas can be prevented while ammonia in the measurement target gas can be prevented from being decomposed by the protective cover 120.

Figure 10:
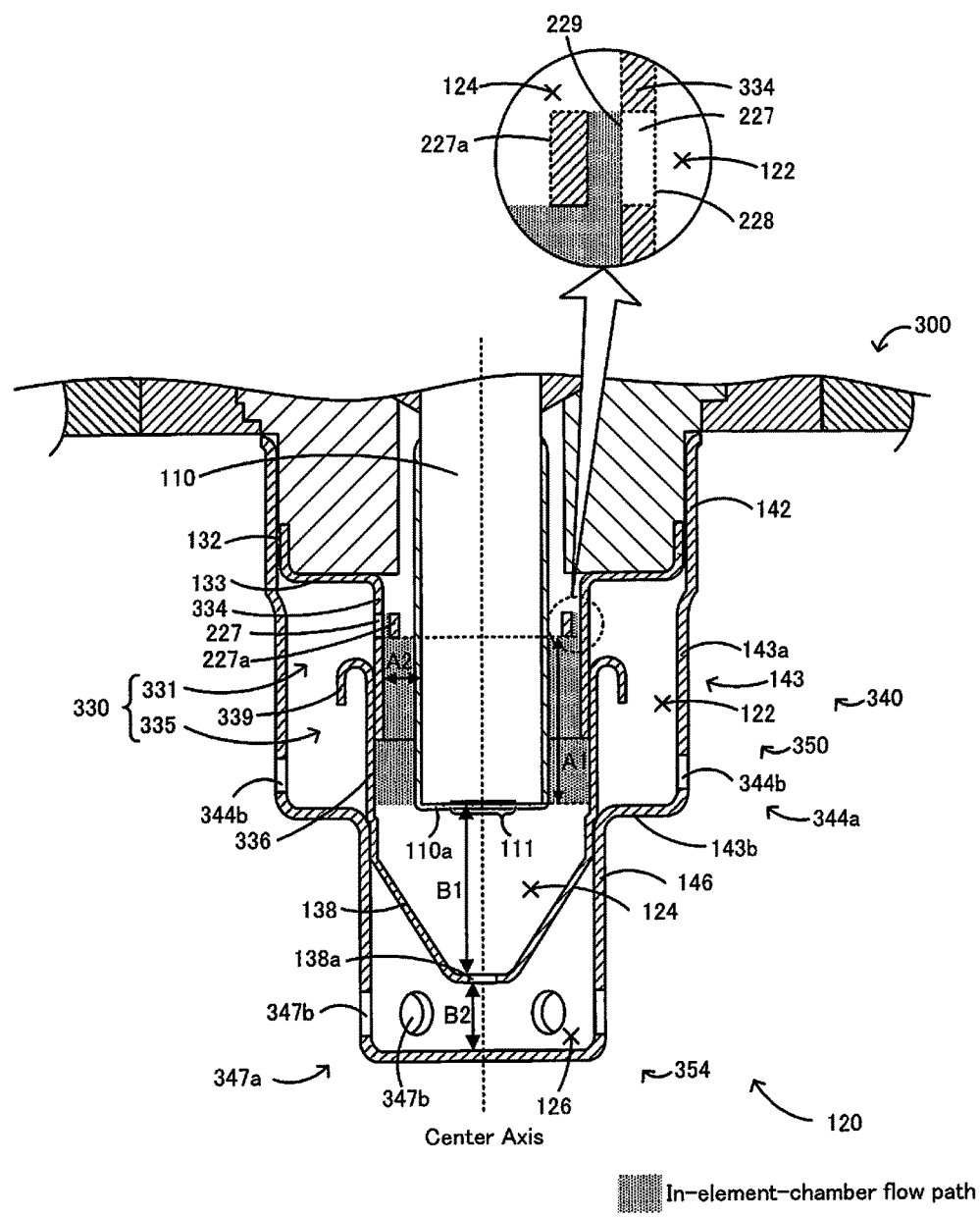
FIG. 10 is a vertical sectional view of a gas sensor 300 according to a modified example.

FIG. 10 is a vertical sectional view of a gas sensor 300 according to a modified example. In FIG. 10, components that are the same as those of the gas sensor 100 or the gas sensor 200 are denoted with the same symbols and are not described in detail. As illustrated in FIG. 10, the gas sensor 300 includes an inner protective cover 330 instead of the inner protective cover 130. The inner protective cover 330 includes a first member 331 and a second member 335. The first member 331 has the same configuration as the first member 131 illustrated in FIG. 3 except that it includes, instead of the first cylindrical portion 134, a first cylindrical portion 334 having a shorter axial length than the first cylindrical portion 134. In the first cylindrical portion 334, multiple, or six, element-chamber inlets 227 and multiple, or six, flow-control members 227a are formed as in the case of the gas sensor 200 illustrated in FIGS. 8 and 9. The second member 335 has the same configuration as the second member 135 illustrated in FIG. 3 except that it includes a second cylindrical portion 336 and a bent-back portion 339 instead of the second cylindrical portion 136 and the connection portion 137. The second cylindrical portion 336 has a smaller diameter than the second cylindrical portion 136 and has its internal circumferential surface abutting the external circumferential surface of the first cylindrical portion 334. Thus, no flow path for the measurement target gas is formed between the first cylindrical portion 334 and the second cylindrical portion 336. The measurement target gas thus flows from the first gas chamber 122 through the element-chamber inlets 227 into the sensor element chamber 124. The bent-back portion 339 has such a shape that the diameter of the upper end portion of the second cylindrical portion 336 is increased and the upper end portion is bent downward. The bent-back portion 339 has a function of preventing water or other substances that has flowed into the first gas chamber 122 from flowing into the sensor element chamber 124. An outer protective cover 340 has the same configuration as the outer protective cover 140 except that it has outer inlets 344a and outer outlets 347a instead of the outer inlets 144a and the outer outlets 147a. The outer inlets 344a have no vertical holes and include multiple, or six, horizontal holes 344b equidistantly formed in the barrel 143. The outer outlets 347a have no vertical holes and include multiple, or six, horizontal holes 347b equidistantly formed in the side surface of the front end portion 146. As illustrated in FIG. 10, the distance A1 in the gas sensor 300 according to the modified example is a distance from the gas inlet 111 to the lower end of the element-side openings 229 in the vertical direction. The protective cover 120 defines an inlet-side gas flow path 350 constituted by the outer inlets 344a, the first gas chamber 122, and the element-chamber inlets 227. The sum of the areas of portions of the inner protective cover 330 and the outer protective cover 340 facing the inlet-side gas flow path 350 is determined as the surface area S1. The shortest flow path in the sensor element chamber 124 for the measurement target gas from the upper end of the element-chamber inlets 227, or the element-side openings 229, to the gas inlet 111 is determined as an in-element-chamber flow path 352 (see the hatched portion in FIG. 10). The sum of the areas of portions of the inner protective cover 330 facing the in-element-chamber flow path 352 is determined as the surface area S2. In the enlarged view in the upper right of FIG. 10, a portion of the inner protective cover 330 facing the in-element-chamber flow path 352 is drawn with the solid line and other portions are drawn with the broken lines. As is clear from the enlarged view in the upper right of FIG. 10, the surface area S2 includes the areas of the surfaces or the control surfaces of the flow-control members 227a facing the element-chamber inlets 227 and the areas of the undersurfaces of the flow-control members 227a. The protective cover 120 defines an outlet-side gas flow path 254 constituted by the element-chamber outlet 138a, the second gas chamber 126, and the outer outlets 347a. The gas sensor 300 having the above-described configuration can also attain the same effects since it has the similar features to the above-described embodiment. For example, when the gas-contact surface area S is determined to fall within the range of 450 mm$^2$ to 1145 mm$^2$, the failures resulting from simplifying the path for the measurement target gas can be prevented while ammonia in the measurement target gas can be prevented from being decomposed by the protective cover 120.

Not only the gas sensors 200 and 300 described above, the shape of the protective cover 120 or the shape, the number, the location, or other parameters of the element-chamber inlet 127, the element-chamber outlet 138a, the outer inlets 144a, or the outer outlets 147a may be appropriately changed. For example, the element-chamber inlet 127 is described as a gap between the first member 131 and the second member 135. However, the element-chamber inlet 127 is not limited to this configuration: the element-chamber inlet may have any shape as long as it serves as an inlet to the sensor element chamber 124. For example, the element-chamber inlet may be a through hole formed in the inner protective cover 130. In the case where the element-chamber inlet is a through hole, the element-chamber inlet may form a flow path from the rear end toward the front end of the sensor element 110. For example, the element-chamber inlet may be a vertical hole or a hole inclined with respect to the vertical direction in FIG. 3. The number of element-chamber inlets is not limited to one and may be two or more. Moreover, the element-chamber outlet 138a, outer inlets 144a, and outer outlets 147a are not limited to holes and may be gaps between multiple components of the protective cover 120. The number of element-chamber outlet 138a, outer inlets 144a, or outer outlets 147a may be one or more. The outer inlets 144a have been described as including the horizontal holes 144b and the vertical holes 144c. However, the outer inlets may only include either the horizontal holes 144b or the vertical holes 144c. In addition to or instead of the horizontal holes 144b and the vertical holes 144c, corner holes may be formed at the corner portions on the boundary of the side portion 143a and the stepped portion 143b. Similarly, the element-chamber inlet 127, the element-chamber outlet 138a, and the outer outlets 147a may be any one or more horizontal holes, one or more vertical holes, or one or more corner holes.

In the above-described embodiment, the protrusions 136a are provided on the internal circumferential surface of the second cylindrical portion 136, but this is not the only possible configuration. Multiple protrusions will suffice if they are disposed on at least one of the external circumferential surface of the first cylindrical portion 134 and the internal circumferential surface of the second cylindrical portion 136 so as to protrude toward the opposing surface and abut the surface. In the above-described embodiment, as illustrated in FIGS. 3 to 5, portions of the external circumferential surface of the second cylindrical portion 136 at which the protrusions 136a are formed are recessed inward. However, the external circumferential surface does not have to be recessed. Furthermore, the protrusions 136a are not limited to have a hemisphere shape and may have any shape. The protrusions 136a do not have to be disposed on the external circumferential surface of the first cylindrical portion 134 or the internal circumferential surface of the second cylindrical portion 136.

Figure 11:
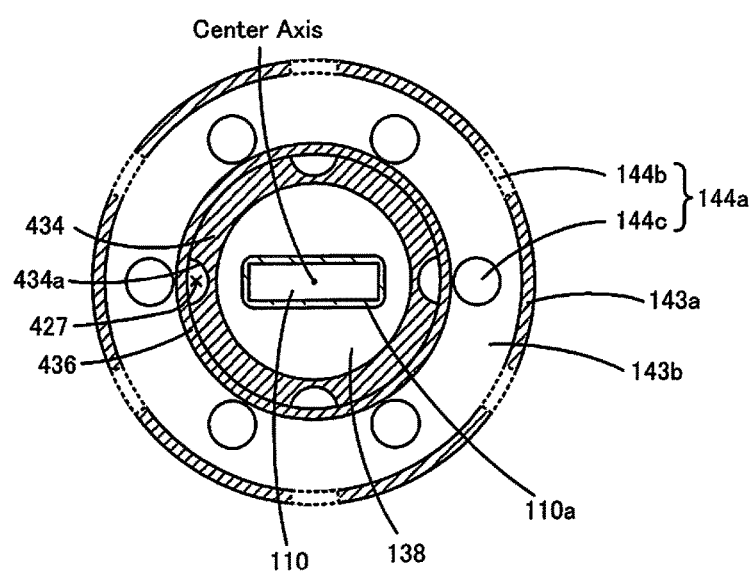
FIG. 11 is a cross-sectional view of an element-chamber inlet 427 according to a modified example.

In the above-described embodiment, the element-chamber inlet 127 is described as a cylindrical gap between the external circumferential surface of the first cylindrical portion 134 and the internal circumferential surface of the second cylindrical portion 136, but this is not the only possible configuration. For example, a recess or a groove may be formed in at least one of an external circumferential surface of a first cylindrical portion and an internal circumferential surface of a second cylindrical portion and the element-chamber inlet may be a gap between the first cylindrical portion and the second cylindrical portion formed by the recess. FIG. 11 is a cross-sectional view of an element-chamber inlet 427 according to a modified example. As illustrated in FIG. 11, the external circumferential surface of a first cylindrical portion 434 and the internal circumferential surface of a second cylindrical portion 436 touch each other and multiple recesses 434a, four in FIG. 11, are equidistantly formed on the external circumferential surface of the first cylindrical portion 434. These gaps between the recess 434a and the internal circumferential surface of the second cylindrical portion 436 serve as the element-chamber inlets 427.

Figure 12:
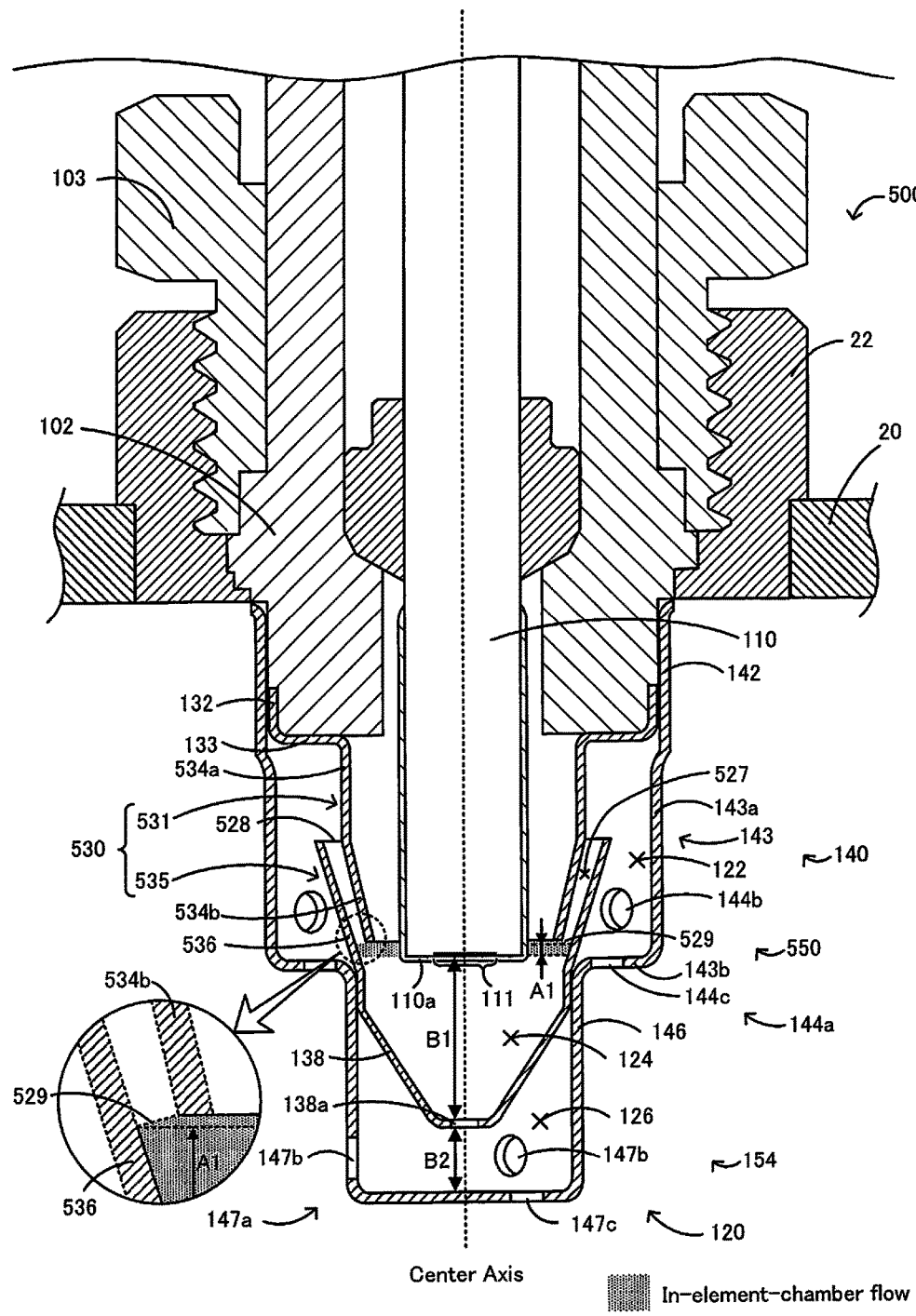
FIG. 12 is a vertical sectional view of a gas sensor 500 according to this modified example.

In the above-described embodiment, the element-chamber inlets 127 are flow paths parallel to the direction connecting the rear end and the front end of the sensor element 110, or vertical flow paths in FIG. 3, but this is not the only possible configuration. For example, the element-chamber inlets may be flow paths that are inclined with respect to the direction connecting the rear end and the front end so as to increasingly come closer to the sensor element 110 from the rear end to the front end of the sensor element 110. FIG. 12 is a vertical sectional view of a gas sensor 500 according to this modified example. In FIG. 12, components that are the same as those in the gas sensor 100 are denoted by the same symbols and are not described in detail. As illustrated in FIG. 12, the gas sensor 500 includes an inner protective cover 530 instead of the inner protective cover 130. The inner protective cover 530 includes a first member 531 and a second member 535. In contrast to the first member 131, the first member 531 does not include the first cylindrical portion 134 but includes a cylindrical barrel 534a and a first cylindrical portion 534b that has a cylindrical shape whose diameter increasingly tapers from the rear end toward the front end of the sensor element 110. The first cylindrical portion 534b is connected to the barrel 534a at its end closer to the rear end of the sensor element 110. In contrast to the second member 135, the second member 535 does not include the second cylindrical portion 136 and the connection portion 137 but includes a second cylindrical portion 536 that has a cylindrical shape whose diameter increasingly tapers from the rear end toward the front end of the sensor element 110. The second cylindrical portion 536 is connected to the front end portion 138. The external circumferential surface of the first cylindrical portion 534b and the internal circumferential surface of the second cylindrical portion 536 do not touch each other and form a gap therebetween, which serves as an element-chamber inlet 527. The element-chamber inlet 527 includes an outer opening 528, which is an opening located closer to the first gas chamber 122, and an element-side opening 529, which is an opening located closer to the sensor element chamber 124. Due to the shapes of the first cylindrical portion 534b and the second cylindrical portion 536, the element-chamber inlet 527 serves as a flow path inclined with respect to the direction connecting the rear end and the front end so as to increasingly come closer to the sensor element 110, or closer to the center axis of the inner protective cover 530, from the rear end toward the front end of the sensor element 110. Similarly, the element-side opening 529 is open obliquely with respect to the direction connecting the rear end and the front end so as to increasingly come closer to the sensor element 110 from the rear end toward the front end of the sensor element 110 (see an enlarged view in FIG. 12). In this manner, even in the case where the element-chamber inlet 527 is an inclined flow path or the element-side opening 529 is obliquely open, the direction of flow of the measurement target gas that flows into the sensor element chamber 124 from the element-side opening 529 is a direction inclined with respect to the direction connecting the rear end and the front end of the sensor element 110. Thus, the same effects as those of the element-chamber inlet 127 or the element-side opening 129 according to the above-described embodiment can be obtained. Specifically, this configuration can prevent the measurement target gas from vertically coming into contact with the surface of the sensor element 110, that is, a portion of the surface other than the gas inlet 111, or from arriving at the gas inlet 111 after flowing a long distance over the surface of the sensor element 110. Thus, cooling of the sensor element 110 can be prevented. In addition, the width of the element-chamber inlet 527 is increasingly reduced from the rear end toward the front end of the sensor element 110. Thus, the opening area of the element-side opening 529 is smaller than the opening area of the outer opening 528. In other words, in the element-chamber inlet 527, the distance A4 is smaller than the distance A5, described with reference to FIG. 4. This configuration enhances the flow rate of the measurement target gas at the time when the measurement target gas flows out compared to the time when the measurement target gas flows in since the measurement target gas flows in from the outer opening 528 and flows out from the element-side opening 529. This configuration can thus improve the responsivity of gas concentration detection. Here, the element-chamber inlet 527 does not necessarily need to be inclined with respect to the direction connecting the rear end and the front end of the sensor element 110. As long as the opening area of the element-side opening 529 is formed smaller than the opening area of the outer opening 528, the configuration attains a responsivity enhancement effect.

As illustrated in FIG. 12, the distance A1 in the gas sensor 500 according to the modified example is a vertical distance from the gas inlet 111 to the lower end of the element-side opening 529. The protective cover 120 of the gas sensor 500 defines an inlet-side gas flow path 550 constituted by the outer inlets 144a, the first gas chamber 122, and the element-chamber inlet 527. The sum of the areas of portions of the inner protective cover 530 and the outer protective cover 140 facing the inlet-side gas flow path 550 is determined as the surface area S1. The shortest flow path in the sensor element chamber 124 for the measurement target gas from the upper end of the element-chamber inlet 527, or the element-side opening 529, to the gas inlet 111 serves as an in-element-chamber flow path 552 (see the hatched portion in FIG. 12). The sum of the areas of portions of the inner protective cover 530 facing the in-element-chamber flow path 552 is determined as the surface area S2. In the enlarged view in FIG. 12, a portion of the inner protective cover 530 facing the in-element-chamber flow path 552 is drawn with a solid line and other portions are drawn with broken lines. As is clear from the enlarged view in the upper right of FIG. 12, the surface area S2 includes the area of the undersurface of the first cylindrical portion 534b or the area of a portion of the internal circumferential surface of the second cylindrical portion 536.

Figure 13:
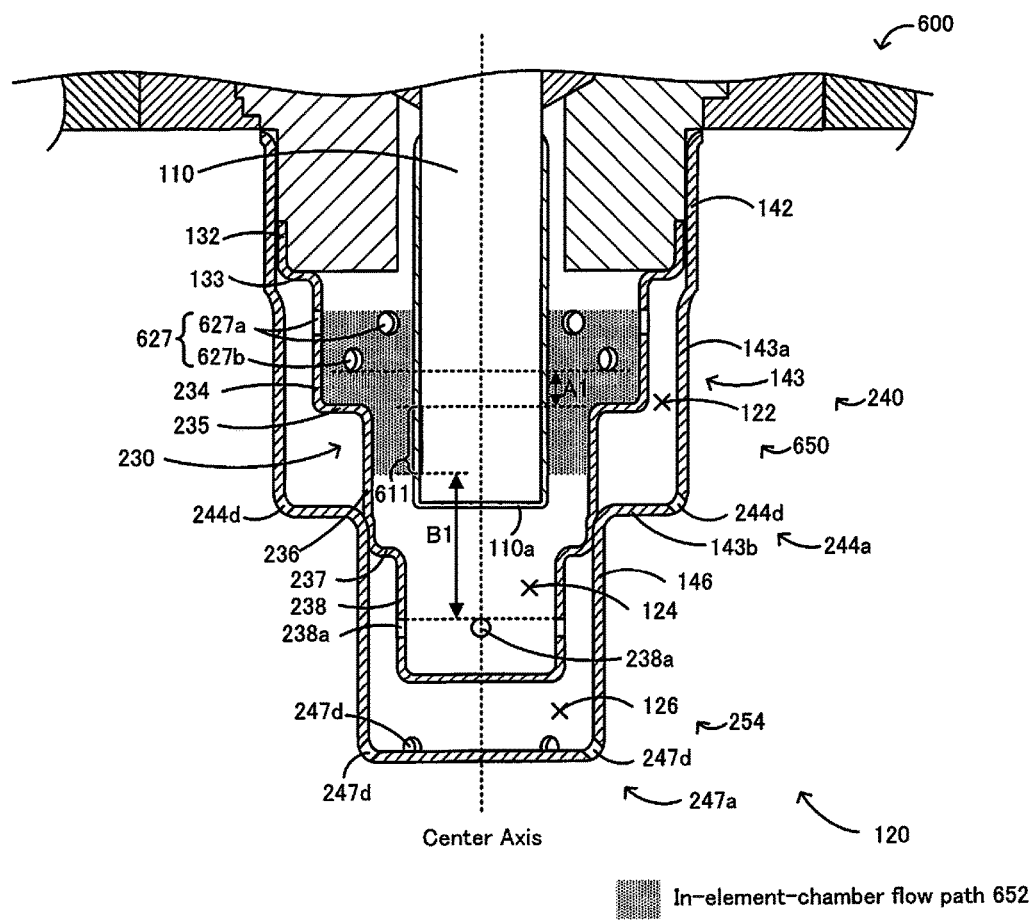
FIG. 13 is a vertical sectional view of a gas sensor 600 according to a modified example.

In the above-described embodiment, the gas inlet 111 is described as being open in the front end surface of the sensor element 110, that is, the undersurface of the sensor element 110 in FIG. 3, but this is not the only possible configuration. For example, the gas inlet 111 may be open in the side surface of the sensor element 110, specifically, the upper, lower, left, or right surface of the sensor element 110 in FIG. 5. In the case where multiple element-chamber inlets are formed in the protective cover 120, for example, the element-chamber inlets 227 of the gas sensor 200 or 300 illustrated in FIG. 8 and FIG. 10, one or more of the multiple element-chamber inlets may be formed at a position displaced from the positions of the other element-chamber inlets in a direction connecting the rear end and the front end of the sensor element 110. FIG. 13 is a vertical sectional view of a gas sensor 600 according to a modified example. In FIG. 13, components that are the same as those in the gas sensor 200 are denoted by the same symbols and are not described in detail. As illustrated in FIG. 13, the gas sensor 600 has the same configuration as the gas sensor 200 illustrated in FIG. 8 except that the sensor element 110 includes a gas inlet 611 open in the side surface instead of the gas inlet 111 and that the inner protective cover 230 includes multiple element-chamber inlets 627 instead of the element-chamber inlets 227 and the flow-control members 227a. The element-chamber inlets 627 are holes communicating with the first gas chamber 122 and the sensor element chamber 124. The element-chamber inlets 627 include multiple upper horizontal holes 627a formed in the first barrel 234 and multiple lower horizontal holes 627b formed in the first barrel 234 at positions closer to the front end of the sensor element 110, or lower in FIG. 13, than to the upper horizontal holes 627a. As illustrated in FIG. 13, the distance A1 in the gas sensor 600 according to the modified example is a vertical distance from the lower end of the lower horizontal holes 627b to the upper end of the gas inlet 611. The distance B1 is a vertical distance from the lower end of the gas inlet 611 to the upper end of the element-chamber outlets 238a. The protective cover 120 of the gas sensor 600 defines an inlet-side gas flow path 650 constituted with the outer inlets 244a, the first gas chamber 122, and the element-chamber inlets 627, that is, the upper horizontal holes 627a and the lower horizontal holes 627b. The sum of the areas of the portions of an inner protective cover 630 and the outer protective cover 240 facing the inlet-side gas flow path 650 is determined as the surface area S1. The shortest flow path in the sensor element chamber 124 for the measurement target gas from the upper end of the element-chamber inlets 627, that is, the upper end of the upper horizontal holes 627a, to the lower end of the gas inlet 611 serves as an in-element-chamber flow path 652 (see the hatched portion in FIG. 13). The sum of the areas of portions of the inner protective cover 630 facing the in-element-chamber flow path 652 is determined as the surface area S2.

In the above-described embodiment, the protective cover 120 has been described as including the inner protective cover 130 and the outer protective cover 140, but this is not the only possible configuration. The protective cover 120 will suffice if it defines a sensor element chamber, in which the front end of the sensor element 110 and the gas inlet 111 are disposed, and an inlet-side gas flow path, which extends from the outside to the sensor element chamber and includes at least one element-chamber inlet serving as an inlet to the sensor element chamber. For example, the protective cover 120 may include, beside the inner protective cover 130 and the outer protective cover 140, an intermediate protective cover interposed between the inner protective cover 130 and the outer protective cover 140.

In the above-described embodiment, the distance A1 is −1.5 mm or more and the element-chamber outlet 138a is formed at a position closer to the front end of the sensor element 110 than to the gas inlet 111, that is, the distance B1 is smaller than 0 mm, but this is not the only possible configuration. For example, the element-chamber inlet 127 or the element-side opening 129 may be formed at a position at which the distance A1 is smaller than −1.5 mm or at which the distance A1 is −5 mm or more and 1.5 mm or less. Nevertheless, in terms of smooth flow of the measurement target gas and prevention of ammonia in the measurement target gas from being decomposed by the protective cover 120, the distance A1 is preferably −1.5 mm or more and the distance B1 is preferably smaller than 0 mm.

In the above-described embodiment, the protective cover 120 is formed of a metal containing at least one of chromium or nickel, such as stainless steel, but this is not the only possible configuration. The protective cover 120 will suffice if it contains a substance having a capability of decomposing ammonia. The inner protective cover 130 and the outer protective cover 140 will suffice if they each contain a substance having a capability of decomposing ammonia and they may be formed of different materials. Similarly, the first member 131 and the second member 135 may be formed of different materials.

In the above-described embodiment, the sensor element 110 includes the porous protective layer 110a. However, the porous protective layer 110a may be omitted.

In the above-described embodiment, the sensor element 110 converts ammonia into NOx and produces an electric signal corresponding to the concentration of converted NOx so as to detect the ammonia concentration, but this is not the only possible configuration. For example, the sensor element 110 may acquire the ammonia concentration by decomposing ammonia inside itself to produce $H_2$ and $N_2$, pumping out the produced $H_2$ using a proton pump (see the paragraphs 0103 and 0104 in Japanese Patent No. 3511468), and detecting the pump current at that time. In the above-described embodiment, the sensor element 110 has a function of detecting the ammonia concentration in the measurement target gas, but this is not the only possible configuration. The sensor element 110 will suffice if it has a function of detecting the predetermined gas concentration in the measurement target gas. For example, the sensor element 110 may have a function of detecting the NOx concentration or the oxygen concentration in the measurement target gas. In the case where the sensor element 110 detects the NOx concentration, the detection accuracy is lowered when NOx occurs as a result of ammonia in the measurement target gas being decomposed before the measurement target gas arrives at the gas inlet 111. In the case where the sensor element 110 detects the oxygen concentration, the detection accuracy is lowered when oxygen in the measurement target gas is consumed as a result of ammonia in the measurement target gas being decomposed before the measurement target gas arrives at the gas inlet 111. Thus, even in the case where the sensor element 110 detects the NOx concentration or the oxygen concentration, as in the case of the above-described embodiment, ammonia can be prevented from being decomposed by the protective cover 120, whereby the accuracy of detection of the measurement target gas can be prevented from being lowered.

EXAMPLES

Hereinbelow, specifically fabricated examples of a gas sensor are described as experimental examples. Experimental Examples 2 to 5 and 8 to 12 correspond to examples of the invention and Experimental Examples 1, 6, and 7 correspond to comparative examples. The present invention is not limited to the examples described below.

Experimental Example 1

A gas sensor that does not include the protective cover 120 of the gas sensor 100 illustrated in FIGS. 3 to 7 was used as Experimental Example 1.

Experimental Example 2

The gas sensor 100 illustrated in FIGS. 3 to 7 was used as Experimental Example 2. Specifically, the first member 131 of the inner protective cover 130 had a plate thickness of 0.3 mm and an axial length of 10.2 mm, the large-diameter portion 132 had an axial length of 1.8 mm and an outer diameter of 14.4 mm, and the first cylindrical portion 134 had an axial length of 8.4 mm and an outer diameter of 7.7 mm. The second member 135 had a plate thickness of 0.3 mm and an axial length of 11.5 mm, the second cylindrical portion 136 had an axial length of 4.5 mm and an inner diameter of 9.7 mm, and the front end portion 138 had an axial length of 4.9 mm and a bottom surface having a diameter of 3.0 mm. With respect to the element-chamber inlet 127, the distance A1 was 0.59 mm, the distance A2 was 1.5 mm, the distance A3 was 3.1 mm, the distances A4, A5, and A7 were 1.0 mm, the distance A6 was 1.2 mm, and the distance L was 4 mm. The cross-sectional area G2 was 22.3 mm$^2$. The element-chamber outlet 138a had a diameter of 1.5 mm. The distance B1 was −6.3 mm where the cross-sectional area G3=1.77 mm$^2$. The outer protective cover 140 had a plate thickness of 0.4 mm and an axial length of 24.35 mm, the large-diameter portion 142 had an axial length of 5.85 mm and an outer diameter of 15.2 mm, the barrel 143 had an axial length of 8.9 mm, that is, an axial length from the upper end of the barrel 143 to the upper surface of the stepped portion 143b is 8.5 mm, and an outer diameter of 14.6 mm, and the front end portion 146 had an axial length of 9.6 mm and an outer diameter of 8.7 mm. The outer inlets 144a were formed so as to include six horizontal holes 144b having a diameter of 1 mm and six vertical holes 144c having a diameter of 1 mm, which were alternately arranged at equal intervals so that the angle between adjacent holes was 30°, where the cross-sectional area G1=9.42 mm$^2$. The outer outlets 147a were formed so as to include three horizontal holes 147b having a diameter of 1 mm and three vertical holes 147c having a diameter of 1 mm, which were alternately arranged at equal intervals so that the angle between adjacent holes was 60°, where the cross-sectional area G4=4.71 mm$^2$. The distance B2 was 2.7 mm. The material of the protective cover 120 was SUS301S. The surface area S1 was 1052.78 mm$^2$, the surface area S2 was 24.94 mm$^2$, and the gas-contact surface area S was 1077.22 mm$^2$. The area ratio α was 19.7. The sensor element 110 of the gas sensor 100 had a width, or a lateral dimension in FIG. 5, of 4 mm and a thickness, or a vertical dimension in FIG. 5, of 1.5 mm. The porous protective layer 110a was an alumina porous material and had a thickness of 400 μm.

Experimental Example 3

A gas sensor 100 having the same configuration as Experimental Example 2 except that the second cylindrical portion 136 has an axial length longer than that of Experimental Example 2 by 1 mm, that is, has an axial length of 5.5 mm, was used as Experimental Example 3. Herein, the distance A3 was 4.1 mm, the distance L was 5 mm, the surface area S1 was 1115.58 mm$^2$, and the gas-contact surface area S was 1140.52 mm$^2$.

Experimental Example 4

A gas sensor 100 having the same configuration as Experimental Example 2 except that the second cylindrical portion 136 has an axial length shorter than that of Experimental Example 2 by 1 mm, that is, has an axial length of 3.5 mm, was used as Experimental Example 4. Herein, the distance A3 was 2.1 mm, the distance L was 3 mm, the surface area S1 was 989.98 mm$^2$, and the gas-contact surface area S was 1014.92 mm$^2$.

Experimental Example 5

A gas sensor 100 having the same configuration as Experimental Example 2 except that the second cylindrical portion 136 does not include the protrusions 136a, the second cylindrical portion 136 has an axial length of 2.1 mm, the housing 102 has a longer axial length, the large-diameter portion 142 has a longer axial length, that is, 8.6 mm, and the barrel 143 has a shorter axial length, that is, the axial length from the upper end of the barrel 143 to the upper surface of the stepped portion 143b is 6.2 mm, was used as Experimental Example 5. Herein, the distance A3 was 0.25 mm, the distance L was 1.5 mm, the surface area S1 was 789.93 mm$^2$, and the gas-contact surface area S was 814.87 mm$^2$.

Experimental Example 6

The gas sensor 200 illustrated in FIG. 8 was used as Experimental Example 6. Specifically, the inner protective cover 230 had an axial length of 17.7 mm, the first barrel 234 had an axial length of 5.4 mm and an outer diameter of 11.8 mm, the second barrel 236 had an axial length of 5.6 mm and an outer diameter of 8.2 mm, and the front end portion 238 had an axial length of 4.9 mm and an outer diameter of 5.9 mm. The external opening area of each of the six element-chamber inlets 227 was 0.396 mm$^2$, where the cross-sectional area G2=2.38 mm$^2$. The distance A1 was 6.2 mm, the distance A2 was 3.6 mm, and the distance A6 was 1.8 mm. An angle θ1 between the control surface of the flow-control member 227a and the outer opening surface of the element-chamber inlet 227 was 38°. The vertical height of the flow-control member 227a, that is, the vertical height of FIG. 8, was 1.15 mm. The element-chamber outlets 238a were horizontal holes having a diameter of 1 mm where the cross-sectional area G3=3.14 mm$^2$. In the outer protective cover 240, six corner holes 244d having a diameter of 1 mm were equidistantly formed as the outer inlets 244a, where the cross-sectional area G1=4.71 mm$^2$, and six corner holes 247d having a diameter of 1.2 mm were equidistantly formed as the outer outlets 247a, where the cross-sectional area G4=6.78 mm$^2$. The distance B1 was −5.7 mm and the distance B2 was 2.7 mm. The surface area S1 was 868.67 mm$^2$, the surface area S2 was 281.15 mm$^2$, and the gas-contact surface area S was 1149.82 mm$^2$. The area ratio α was 10.74. Other portions were similarly formed as in the case of Experimental Example 2.

Experimental Example 7

The gas sensor 300 illustrated in FIG. 10 was used as Experimental Example 7. Specifically, in the inner protective cover 330, the first cylindrical portion 334 had an axial length of 5.4 mm and an outer diameter of 7.70 mm, the second member 335 had an axial length of 5.75 mm, the second cylindrical portion 336 had an outer diameter of 8.23 mm, and the bent-back portion 339 had an axial length of 1.8 mm and an outer diameter of R0.6 mm. The six element-chamber inlets 227 had the same external opening area where the cross-sectional area G2=2.87 mm$^2$. The distance A1 was 6.0 mm and the distance A2 (=distance A6) was 1.8 mm. An angle θ1 between the control surface of the flow-control member 227a and the outer opening surface of the element-chamber inlet 227 was 38°. The vertical height of the flow-control member 227a, that is, the vertical height of FIG. 8, was 1.15 mm. The element-chamber outlet 138a was a horizontal hole having a diameter of 1 mm, where the cross-sectional area G3=0.79 mm$^2$. In the outer protective cover 340, six horizontal holes 344b having a diameter of 1 mm were equidistantly formed as outer inlets 344a, where the cross-sectional area G1=4.71 mm$^2$, and six horizontal holes 347b having a diameter of 1 mm were equidistantly formed as outer outlets 347a, where the cross-sectional area G4=4.71 mm². The distance B1 was −6.3 mm and the distance B2 was 2.6 mm. The surface area S1 was 972.57 mm², the surface area S2 was 178.14 mm², and the gas-contact surface area S was 1150.72 mm². The area ratio α was 2.25. Other components were similarly formed as in the case of Experimental Example 2.

Experimental Example 8

A gas sensor 100 having the same configuration as Experimental Example 2 except that the outer inlets 144a and the outer outlets 147a have the same diameter of 0.8 mm was used as Experimental Example 8. Herein, the distance A3 was 3.0 mm, the surface area S1 was 1053.16 mm², the gas-contact surface area S was 1078.10 mm², the cross-sectional area G1 was 6.03 mm², and the cross-sectional area G4 was 3.01 mm². The area ratio α was 19.7.

Experimental Example 9

A gas sensor 100 having the same configuration as Experimental Example 2 except that the outer inlets 144a and the outer outlets 147a have the same diameter of 1.2 mm was used as Experimental Example 9. Herein, the distance A3 was 3.2 mm, the surface area S1 was 1051.65 mm², the gas-contact surface area S was 1076.59 mm², the cross-sectional area G1 was 13.56 mm², the cross-sectional area G4 was 6.78 mm², and the area ratio α was 19.7.

Experimental Example 10

A gas sensor 100 having the same configuration as Experimental Example 2 except that the distances A4, A5, and A7 in the inner protective cover 130 are 1.5 mm and except that the second cylindrical portion 136 does not include the protrusions 136a was used as Experimental Example 10. Herein, the surface area S1 was 1028.29 mm², the surface area S2 was 24.00 mm², the gas-contact surface area S was 1052.29 mm², the cross-sectional area G1 was 9.42 mm², the cross-sectional area G2 was 38.64 mm², the cross-sectional area G3 was 1.77 mm², the cross-sectional area G4 was 4.71 mm², and the area ratio α was 34.20.

Experimental Example 11

A gas sensor 100 having the same configuration as Experimental Example 2 except that the distances A4, A5, and A7 in the inner protective cover 130 are 0.5 mm and except that the second cylindrical portion 136 does not include the protrusions 136a was used as Experimental Example 10. Herein, the surface area S1 was 1056.87 mm², the surface area S2 was 25.89 mm², the gas-contact surface area S was 1082.76 mm², the cross-sectional area G1 was 9.42 mm², the cross-sectional area G2 was 14.45 mm², the cross-sectional area G3 was 1.77 mm², the cross-sectional area G4 was 4.71 mm², and the area ratio α was 12.79.

Experimental Example 12

A gas sensor 100 having the same configuration as Experimental Example 2 except that the first cylindrical portion 134 has an axial length shorter than that of Experimental Example 2 by 0.5 mm, that is, has an axial length of 7.9 mm, and has outer diameter larger than that of Experimental Example 2 by 0.5 mm, that is, has an outer diameter of 8.2 mm was used as Experimental Example 12. Herein, the distance A1 was 1.1 mm, the distance A4, A5, and A7 were 0.75 mm, the surface area S1 was 1042.74 mm², the surface area S2 was 40.95 mm², the gas-contact surface area S was 1083.69 mm², the cross-sectional area G2 was 17.20 mm², and the area ratio α was 15.22.

Table 1 collectively shows, regarding Experimental Examples 1 to 12, the values at the inlet and outlet of the outer protective cover and the inner protective cover, the surface area S1, the surface area S2, the gas-contact surface area S, the distance A1, the distance B1, the cross-sectional areas G1 to G4, and the area ratio α.

TABLE 1

| | Outer Protective Cover | | Inner Protective Cover | | Surface Area S1 [mm²] | Surface Area S2 [mm²] | Gas-contact Surface Area S [mm²] | Distance A1 (mm) | Distance B1 (mm) |
|---|---|---|---|---|---|---|---|---|---|
| | Outer Inlets | Outer Outlets | Element-chamber Inlets | Element-chamber Outlets | | | | | |
| Experimental Example 1 | — | — | — | — | 0.0 | 0.0 | 0 | — | — |
| Experimental Example 2 | Diameter 1 mm × 6 (Horizontal Hole) Diameter 1 mm × 6 (Vertical Hole) | Diameter 1 mm × 3 (Horizontal Hole) Diameter 1 mm × 3 (Vertical Hole) | Cylindrical Gap | Vertical Hole (Diameter 1.5 mm × 1) | 1052.78 | 24.94 | 1077.72 | 0.59 | −6.3 |
| Experimental Example 3 | Diameter 1 mm × 6 (Horizontal Hole) Diameter 1 mm × 6 (Vertical Hole) | Diameter 1 mm × 3 (Horizontal Hole) Diameter 1 mm × 3 (Vertical Hole) | Cylindrical Gap | Vertical Hole (Diameter 1.5 mm × 1) | 1115.58 | 24.94 | 1140.52 | 0.59 | −6.3 |
| Experimental Example 4 | Diameter 1 mm × 6 (Horizontal Hole) Diameter 1 mm × 6 (Vertical Hole) | Diameter 1 mm × 3 (Horizontal Hole) Diameter 1 mm × 3 (Vertical Hole) | Cylindrical Gap | Vertical Hole (Diameter 1.5 mm × 1) | 989.98 | 24.94 | 1014.92 | 0.59 | −6.3 |
| Experimental Example 5 | Diameter 1 mm × 6 (Horizontal Hole) Diameter 1 mm × 6 (Vertical Hole) | Diameter 1 mm × 3 (Horizontal Hole) Diameter 1 mm × 3 (Vertical Hole) | Cylindrical Gap | Vertical Hole (Diameter 1.5 mm × 1) | 789.93 | 24.94 | 814.87 | 0.59 | −6.3 |
| Experimental Example 6 | Diameter 1 mm × 6 (Corner Hole) | Diameter 1.2 mm × 6 (Corner Hole) | Six Horizontal Holes | Horizontal Hole (Diameter | 868.67 | 281.15 | 1149.82 | 6.20 | −5.7 |

TABLE 1-continued

| | | | | | | | | | |
|---|---|---|---|---|---|---|---|---|---|
| Experimental Example 7 | Diameter 1 mm × 6 (Horizontal Hole) | Diameter 1 mm × 6 (Horizontal Hole) | Six Horizontal Holes with Flow-Control Member (Diameter 1 mm × 4) | Vertical Hole (Diameter 1 mm × 1) | 972.57 | 178.14 | 1150.72 | 6.00 | −6.3 |
| Experimental Example 8 | Diameter 0.8 mm × 6 (Horizontal Hole) Diameter 0.8 mm × 6 (Vertical Hole) | Diameter 0.8 mm × 3 (Horizontal Hole) Diameter 0.8 mm × 3 (Vertical Hole) | Cylindrical Gap | Vertical Hole (Diameter 1.5 mm × 1) | 1053.16 | 24.94 | 1078.10 | 0.59 | −6.3 |
| Experimental Example 9 | Diameter 1.2 mm × 6 (Horizontal Hole) Diameter 1.2 mm × 6 (Vertical Hole) | Diameter 1.2 mm × 3 (Horizontal Hole) Diameter 1.2 mm × 3 (Vertical Hole) | Cylindrical Gap | Vertical Hole (Diameter 1.5 mm × 1) | 1051.65 | 24.94 | 1076.59 | 0.59 | −6.3 |
| Experimental Example 10 | Diameter 1 mm × 6 (Horizontal Hole) Diameter 1 mm × 6 (Vertical Hole) | Diameter 1 mm × 3 (Horizontal Hole) Diameter 1 mm × 3 (Vertical Hole) | Cylindrical Gap | Vertical Hole (Diameter 1.5 mm × 1) | 1028.29 | 24.00 | 1052.29 | 0.59 | −6.3 |
| Experimental Example 11 | Diameter 1 mm × 6 (Horizontal Hole) Diameter 1 mm × 6 (Vertical Hole) | Diameter 1 mm × 3 (Horizontal Hole) Diameter 1 mm × 3 (Vertical Hole) | Cylindrical Gap | Vertical Hole (Diameter 1.5 mm × 1) | 1056.87 | 25.89 | 1082.76 | 0.59 | −6.3 |
| Experimental Example 12 | Diameter 1 mm × 6 (Horizontal Hole) Diameter 1 mm × 6 (Vertical Hole) | Diameter 1 mm × 3 (Horizontal Hole) Diameter 1 mm × 3 (Vertical Hole) | Cylindrical Gap | Vertical Hole (Diameter 1.5 mm × 1) | 1042.74 | 40.95 | 1083.69 | 1.1 | −6.3 |

| | Cross-sectional Area G1 [mm²] | Cross-sectional Area G2 [mm²] | Cross-sectional Area G3 [mm²] | Cross-sectional Area G4 [mm²] | Area Ratio α | Relative Detection Sensitivity Ratio [%][X1] | Relative Detection Sensitivity Ratio [%][X1] (Maximum Value) | Relative Detection Sensitivity Ratio [%][X1] (Minimum Value) |
|---|---|---|---|---|---|---|---|---|
| Experimental Example 1 | — | — | — | — | — | 100 | — | — |
| Experimental Example 2 | 9.42 | 22.30 | 1.77 | 4.71 | 19.70 | 94.1 | 96.8 | 90.9 |
| Experimental Example 3 | 9.42 | 22.30 | 1.77 | 4.71 | 19.70 | 94.6 | 95.5 | 93.8 |
| Experimental Example 4 | 9.42 | 22.30 | 1.77 | 4.71 | 19.70 | 93.8 | 94.8 | 92.5 |
| Experimental Example 5 | 9.42 | 27.33 | 1.77 | 4.71 | 24.14 | 97 | — | — |
| Experimental Example 6 | 4.71 | 2.38 | 3.14 | 6.78 | 10.74 | 83.2 | 89.1 | 72.4 |
| Experimental Example 7 | 4.71 | 2.87 | 0.79 | 4.71 | 2.25 | 78.2 | 87.9 | 74.1 |
| Experimental Example 8 | 6.03 | 22.30 | 1.77 | 3.01 | 19.70 | 90.2 | — | — |
| Experimental Example 9 | 13.56 | 22.30 | 1.77 | 6.78 | 19.70 | 96.4 | — | — |
| Experimental Example 10 | 9.42 | 38.64 | 1.77 | 4.71 | 34.20 | 96.4 | — | — |
| Experimental Example 11 | 9.42 | 14.45 | 1.77 | 4.71 | 12.79 | 89.4 | — | — |
| Experimental Example 12 | 9.42 | 17.20 | 1.77 | 4.71 | 15.22 | 93.9 | 95.4 | 93.0 |

[X1]Relative Detection Sensitivity Ratio [%]: A ratio led out of the formula below when the detection sensitivity ratio of Experimental Example 1 is 100%.

$$\text{Detection Sensitivity Ratio} = \frac{\text{Ammonia Detection Sensitivity ( = Output value of the gas sensor in measurement condition 4 − Output value of the gas sensor in measurement condition 3)}}{\text{NOx concentration detection sensitivity ( = Output value of the gas sensor in measurement condition 2 − Output value of the gas sensor in measurement condition 1)}}$$

[Evaluation Test]

In Experimental Examples 1 to 12, the relative detection sensitivity ratio [%] of the ammonia concentration to the NOx concentration detection sensitivity was measured. Specifically, the measurement was performed in the following manner. Firstly, the gas sensor according to Experimental Example 1 was attached to a pipe, having a diameter of 20 mm, in the same manner as illustrated in FIG. 2. Then, gas having measurement condition 1 was caused to flow through the pipe in the same direction as illustrated in FIG. 2 and output values of the gas sensor, that is, electric current values corresponding to the NOx concentration in the sensor element 110, were measured after the output of the gas sensor had been stabilized. Similarly, output values of the gas sensors were measured using gas having measurement conditions 2 to 4. Thereafter, the detection sensitivity ratio was measured using the formula expressed in the margin of Table 1. The detection sensitivity ratio of Experimental Examples 2 to 12 was similarly measured. Table 2 shows the measurement conditions 1 to 4. Table 1 shows the relative detection sensitivity ratio [%], that is, the detection sensitivity ratio of Experimental Examples 1 to 12 when the detection sensitivity ratio of Experimental Example 1 is 100%. The relative detection sensitivity ratio of Experimental Examples 2 to 4, 6, 7, and 12 was derived from the average value of detection sensitivity ratios acquired from plural times of measurement. Table 1 also shows the maximum value and the minimum value of the relative detection sensitivity ratios of Experimental Example 2 to 4, 6, 7, and 12. Here, the numerator in the formula written in the margin of Table 1 decreases further as a larger amount of ammonia in the measurement target gas is decomposed as a result of coming into contact with the protective cover, whereby the detection sensitivity ratio is made smaller. Since Experimental Example 1 does not include a protective cover, ammonia is prevented from being decomposed by the protective cover, whereby the detection sensitivity ratio is maximized. Thus, ammonia in the measurement target gas is regarded as being further prevented from being decomposed by the protective cover as the relative detection sensitivity ratio [%] is closer to 100%, that is, the detection sensitivity ratio of Experimental Example 1.

S. Compared to Experimental Examples 6 and 7, the variance of the relative detection sensitivity ratio was significantly reduced in Experimental Examples 2 to 4, in which the gas-contact surface area S is 1145 $mm^2$ or less.

Figure 15:
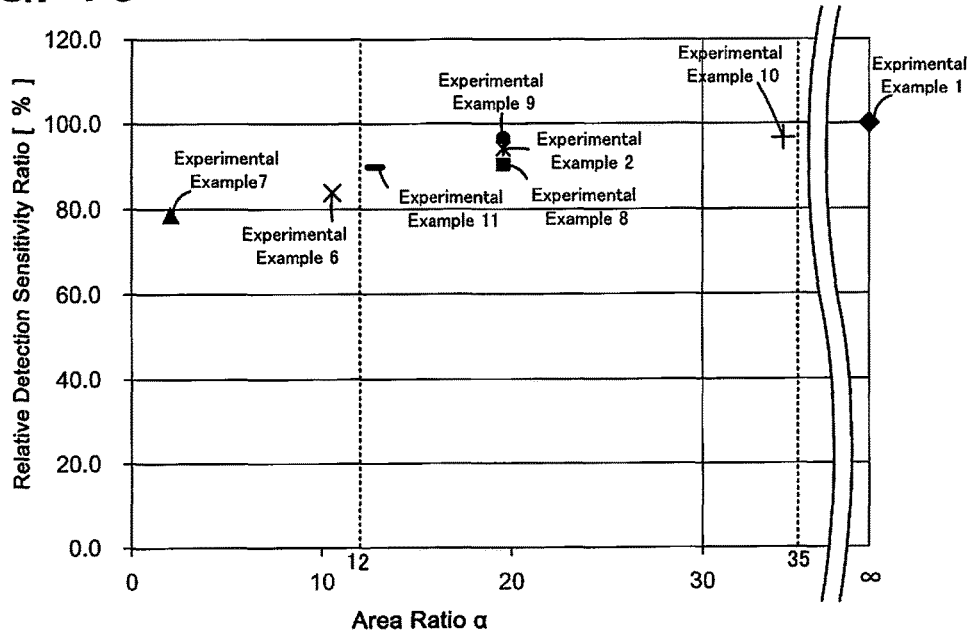
FIG. 15 is a graph showing the relationship between the area ratio α and the relative detection sensitivity ratio [%] of Experimental Examples 1, 2, and 6 to 11.

FIG. 15 is a graph showing the relationship between the area ratio α and the relative detection sensitivity ratio [%] of Experimental Examples 1, 2, and 6 to 11. Although Experimental Example 1 does not have an area ratio α since it does not include a protective cover, the area ratio α of Experimental Example 1 is plotted in FIG. 15 assuming as being equivalent to infinite since the area ratio α is a value expressing how smoothly the measurement target gas flows. As illustrated in FIG. 15, the relative detection sensitivity ratio tended to become close to 100% or to increase with increasing the area ratio α. Particularly, in Experimental Examples 2 and 8 to 11 in which the area ratio α is 12 or more, the relative detection sensitivity ratio was 84% or more, whereby ammonia in the measurement target gas was sufficiently effectively suppressed from being decomposed. From the results of Experimental Examples 2 and 8 to 11, the area ratio α is assumed to be preferably 12 or more and more preferably 12.79 or more, 13 or more, and 18 or more. In addition, the area ratio α is assumed to be preferably 35 or less because if the area ratio α is excessively large, the configuration closely resembles the configuration of Experimental Example 1 that does not include a protective cover, whereby the sensor element 110 is more likely to be cooled to an excessive level due to an excessively high flow rate of

TABLE 2

| | NO [ppm] | $NH_3$ [ppm] | $O_2$ [%] | $H_2O$ [%] | Base Gas | Gas Temperature [° C.] | Gas Flow Rate [L/min] |
|---|---|---|---|---|---|---|---|
| Measurement Condition 1 | 0 | 0 | 0.5 | 3 | $N_2$ | 125 | 200 |
| Measurement Condition 2 | 100 | 0 | 0.5 | 3 | $N_2$ | 125 | 200 |
| Measurement Condition 3 | 0 | 0 | 0.5 | 3 | $N_2$ | 125 | 200 |
| Measurement Condition 4 | 0 | 100 | 0.5 | 3 | $N_2$ | 125 | 200 |

Figure 14:
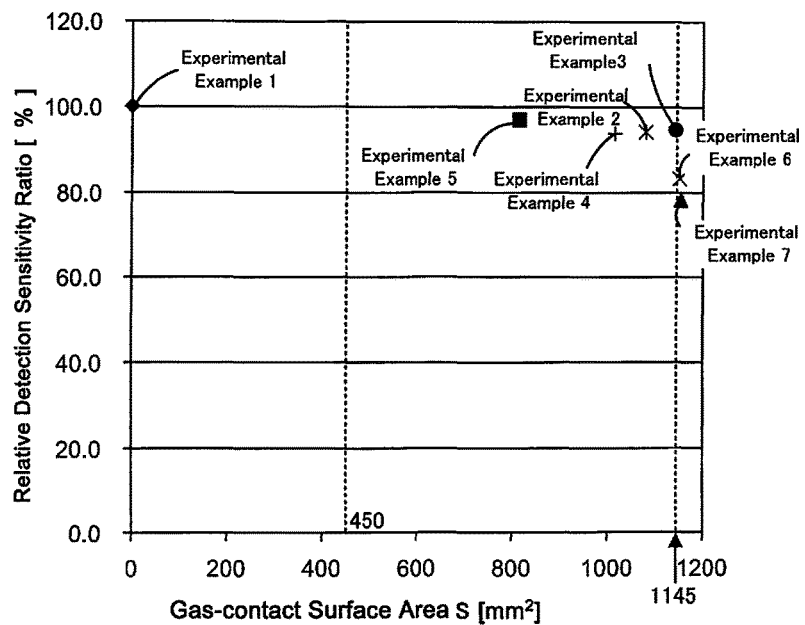
FIG. 14 is a graph showing the relationship between the gas-contact surface area S and the relative detection sensitivity ratio α of Experimental Examples 1 to 7.

FIG. 14 is a graph showing the relationship between the gas-contact surface area S and the relative detection sensitivity ratio [%] of Experimental Examples 1 to 7. As illustrated in FIG. 14, the relative detection sensitivity ratio tended to become closer to 100% or to increase with decreasing gas-contact surface area S. Particularly, in Experimental Examples 2 to 5 in which the gas-contact surface area S is 1145 $mm^2$ or less, the relative detection sensitivity ratio was 84% or more, so that ammonia in the measurement target gas was sufficiently effectively suppressed from being decomposed. In the case where the gas-contact surface area S exceeded 1145 $mm^2$, the relative detection sensitivity ratio tended to decrease suddenly. From these results, the gas-contact surface area S is assumed to be preferably 1145 $mm^2$ or less. The gas-contact surface area S is assumed to be preferably 450 $mm^2$ or more, more preferably 500 $mm^2$ or more, 550 $mm^2$ or more, 600 $mm^2$ or more, or 650 $mm^2$ or more because, if the gas-contact surface area S is excessively small, the configuration closely resembles the configuration of Experimental Example 1 that does not include a protective cover, so that the path for the measurement target gas up to the gas inlet 111 is simplified. When Experimental Examples 2 to 4, 6, and 7 subjected to a plurality of measurements are compared, the variance, that is, the difference between the maximum value and the minimum value, of the relative detection sensitivity ratio tended to decrease with decreasing gas-contact surface area the measurement target gas. The area ratio α is preferably 34.20 or less, more preferably 30 or less, still more preferably 27 or less, and still further more preferably 24 or less. Even when Experimental Examples 2, 8, and 9 having the same area ratio α were compared with one another, the relative detection sensitivity ratio tended to increase with decreasing gas-contact surface area S.

The present application claims priority from Japanese Patent Application No. 2014-244089, filed on Dec. 2, 2014, and Japanese Patent Application No. 2015-235040, filed on Dec. 1, 2015, the entire contents of which are incorporated herein by reference.

What is claimed is:
1. A gas sensor, comprising:
a sensor element that includes a gas inlet through which a measurement target gas is introduced into the sensor element, the sensor element being capable of detecting a predetermined gas concentration of the measurement target gas that has flowed into an inside of the sensor element through the gas inlet; and
a protective cover that contains a substance having a capability of decomposing ammonia, the protective cover defining a sensor element chamber and an inlet-side gas flow path, the sensor element chamber being a chamber in which a front end of the sensor element and the gas inlet are disposed, the inlet-side gas flow path including one or more element-chamber inlets serving as inlets to the sensor element chamber, the inlet-side gas flow path extending from an outside to the sensor element chamber, wherein the protective cover has a gas-contact surface area S within a range of 450 mm² to 1145 mm², the gas-contact surface area S being a sum of a surface area S1 of a portion facing the inlet-side gas flow path and a surface area S2 of a portion facing an in-element-chamber flow path in the sensor element chamber that is a shortest flow path for the measurement target gas from the element-chamber inlet to the gas inlet.

2. The gas sensor according to claim 1, wherein the protective cover defines an outlet-side gas flow path extending to the outside from the sensor element chamber and including one or more element-chamber outlets serving as outlets from the sensor element chamber, and wherein the protective cover has the one or more element-chamber inlets at a position spaced apart from the gas inlet a distance A1 of −1.5 mm or more and the one or more element-chamber outlets at a position located away from the gas inlet in a direction toward a front end from a rear end of the sensor element, where the distance A1 is a distance extending in a direction connecting a rear end and the front end of the sensor element and a direction from the front end to the rear end is regarded as a positive direction.

3. The gas sensor according to claim 1, wherein the protective cover defines an outlet-side gas flow path extending to the outside from the sensor element chamber and including one or more element-chamber outlets serving as outlets from the sensor element chamber and the protective cover includes an inner protective cover and an outer protective cover disposed on an outer side of the inner protective cover, wherein the inner protective cover defines the sensor element chamber, the one or more element-chamber inlets, and the one or more element-chamber outlets, wherein the outer protective cover defines one or more outer inlets, which serve as inlets for the measurement target gas from the outside and constitute part of the inlet-side gas flow path, and one or more outer outlets, which serve as outlets for the measurement target gas to the outside and constitute part of the outlet-side gas flow path, and wherein the outer protective cover and the inner protective cover define a first gas chamber and a second gas chamber, the first gas chamber being a space between the outer protective cover and the inner protective cover and constituting part of the inlet-side gas flow path, the first gas chamber being located between the one or more outer inlets and the one or more element-chamber inlets, the second gas chamber being a space between the outer protective cover and the inner protective cover and constituting part of the outlet-side gas flow path, the second gas chamber being located between the one or more outer outlets and the one or more element-chamber outlets and not directly communicating with the first gas chamber.

4. The gas sensor according to claim 3, wherein an area ratio α falls within a range from 12 to 35, where the area ratio α=a cross-sectional area G2×a cross-sectional area G3×a cross-sectional area G4/a cross-sectional area G1, the cross-sectional area G1 [mm²] is a sum of cross-sectional areas of the one or more outer inlets taken perpendicularly to flow of the measurement target gas, the cross-sectional area G2 [mm²] is a sum of cross-sectional areas of the one or more element-chamber inlets taken perpendicularly to flow of the measurement target gas, the cross-sectional area G3 [mm²] is a sum of cross-sectional areas of the one or more element-chamber outlets taken perpendicularly to flow of the measurement target gas, and the cross-sectional area G4 [mm²] is a sum of cross-sectional areas of the one or more outer outlets taken perpendicularly to flow of the measurement target gas.

5. The gas sensor according to claim 1, wherein the protective cover defines the one or more element-chamber inlets in such a manner that an element-side opening of each of the one or more element-chamber inlets, which is an opening located closer to the sensor element chamber, is open in a direction extending from a rear end to the front end of the sensor element.

6. The gas sensor according to claim 1, wherein the protective cover is formed of a metal containing at least one of chromium and nickel as the substance having a capability of decomposing ammonia.

* * * * *